(12) United States Patent
Balaban et al.

(10) Patent No.: US 6,687,692 B1
(45) Date of Patent: *Feb. 3, 2004

(54) METHOD AND APPARATUS FOR PROVIDING AN EXPRESSION DATA MINING DATABASE

(75) Inventors: David J. Balaban, Cupertino, CA (US); Elina Khurgin, Cupertino, CA (US)

(73) Assignee: Affymetrix, Inc., Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/705,335

(22) Filed: Nov. 2, 2000

Related U.S. Application Data

(62) Division of application No. 09/354,935, filed on Jul. 15, 1999, now Pat. No. 6,185,561.
(60) Provisional application No. 60/100,740, filed on Sep. 17, 1998.

(51) Int. Cl.[7] .............................................. G06F 17/30
(52) U.S. Cl. ............................................ 707/6; 702/20
(58) Field of Search ................................ 707/6; 702/20

(56) References Cited

U.S. PATENT DOCUMENTS

| | | | |
|---|---|---|---|
| 4,683,202 A | 7/1987 | Mullis | 435/91 |
| 5,143,854 A | 9/1992 | Pirrung et al. | 435/518 |
| 5,206,137 A | 4/1993 | Ip et al. | |

(List continued on next page.)

FOREIGN PATENT DOCUMENTS

| | | |
|---|---|---|
| EP | WO 0 307 476 | 3/1989 |
| EP | WO 0 2335 726 | 5/1989 |
| EP | WO 0 392 546 | 10/1990 |
| EP | WO 0 717 113 | 7/1996 |
| WO | WO 90/11548 | 11/1989 |
| WO | WO 90/15070 | 12/1990 |
| WO | WO 92/10588 | 6/1992 |
| WO | WO 93/22456 | 11/1993 |
| WO | WO 95/11995 | 5/1995 |
| WO | WO 96/23078 | 8/1996 |
| WO | WO 97/10365 | 3/1997 |
| WO | WO 97/17317 | 5/1997 |
| WO | WO 97/19410 | 5/1997 |
| WO | WO 97/27317 | 7/1997 |
| WO | WO 97/29212 | 8/1997 |

OTHER PUBLICATIONS

Adams et al., "Complementary DNA Sequencing: Expressed Sequence Tags and Human Genome Project", *Science*, vol. 252, No. 5013, 1995, pps. 1651–1656.

Drmanac, "Sequencing of Megabase Plus DNA by Hybridization: Theory of the Method", *Genomics* 41989, pps. 114–128.

Frickett et al., "Development of a Database for Nucleotide Sequences", *Mathematical Methods for DNA Sequences*, 1989, pps. 2–34.

Gibbs et al., "Detection of single DNA base differences by competitive oligonucleotide priming", *Nucleic Acid Res.*, vol. 17, No. 7, 1989, pps. 2437–2448.

Guatelli et al., "Isothermal, In Vitro Amplification of Nucleic Acids by a Multienzyme Reaction Modeled After Retroviral Replication", *Proc. Natl. Acad. Sci. USA*, vol. 87, No. 5, 1990, pps. 1874–1878.

(List continued on next page.)

*Primary Examiner*—Wayne Amsbury
(74) *Attorney, Agent, or Firm*—Wei Zhou

(57) ABSTRACT

According to the invention, a system and method for organizing expression information in a way that facilitates data mining. A database model is provided which may organize information relating to, e.g., sample preparation, expression analysis of experiment results, and intermediate and final results of mining expression and concentration results. The model is readily translatable into database languages such as SQL and the like. The database model scales to permit mining of expression or concentration information collected from large numbers of samples.

29 Claims, 36 Drawing Sheets

U.S. PATENT DOCUMENTS

| | | | |
|---|---|---|---|
| 5,445,934 A | 8/1995 | Fodor et al. ................... | 435/6 |
| 5,492,806 A | 2/1996 | Drmanac et al. | |
| 5,525,464 A | 6/1996 | Drmanac et al. | |
| 5,571,639 A | 11/1996 | Hubbell et al. ................ | 430/5 |
| 5,593,839 A | 1/1997 | Hubbell et al. ................ | 435/6 |
| 5,642,936 A * | 7/1997 | Evans ........................ | 600/300 |
| 5,667,972 A | 9/1997 | Drmanac et al. ............. | 435/6 |
| 5,695,940 A | 12/1997 | Drmanac et al. ............. | 435/6 |
| 5,700,637 A | 12/1997 | Southern ...................... | 435/6 |
| 5,707,806 A | 1/1998 | Shuber .......................... | 435/6 |
| 5,777,888 A | 7/1998 | Rine et al. .................. | 364/496 |
| 5,800,992 A | 9/1998 | Fodor et al. ................... | 435/6 |
| 5,819,282 A | 10/1998 | Hooper et al. ............. | 707/103 |
| 5,843,669 A | 12/1998 | Kaiser et al. .................. | 435/6 |
| 5,843,767 A | 12/1998 | Beattie ....................... | 435/282 |
| 5,856,101 A | 1/1999 | Hubbell et al. ................ | 435/6 |
| 5,871,697 A | 2/1999 | Rothberg et al. ........... | 382/129 |
| 5,871,928 A | 2/1999 | Fodor et al. ................... | 435/6 |
| 5,899,992 A * | 5/1999 | Iyer et al. ...................... | 707/7 |
| 5,925,525 A | 7/1999 | Fodor et al. ................... | 435/6 |
| 5,961,923 A | 10/1999 | Nova et al. ................ | 422/68.1 |
| 5,974,164 A | 10/1999 | Chee ........................ | 382/129 |
| 5,991,766 A | 11/1999 | Sadiq et al. ................ | 707/103 |
| 6,032,151 A | 2/2000 | Arnold et al. ............. | 707/103 |
| 6,040,138 A | 3/2000 | Lockhart et al. ............... | 435/6 |
| 6,060,240 A | 3/2000 | Kamb et al. .................... | 435/6 |
| 6,046,002 A | 4/2000 | Davis et al. .................... | 435/6 |
| 6,140,054 A | 10/2000 | Wittwer et al. ................ | 435/6 |
| 6,185,561 B1 * | 2/2001 | Balaban et al. ................ | 707/6 |
| 6,229,911 B1 * | 5/2001 | Balaban et al. ............ | 382/128 |
| 6,308,170 B1 * | 10/2001 | Balaban ......................... | 707/3 |
| 6,618,852 B1 * | 9/2003 | van Eikeren et al. ....... | 717/108 |
| 2001/0014734 A1 * | 8/2001 | Fisher ....................... | 536/23.1 |

OTHER PUBLICATIONS

Gusella, "DNA Polymorphism and Human Disease", *Ann. Rev. Biochem.*, vol. 55, 1986, pps. 831–854.

Hara et al., "Subtractive cDNA cloning using oligo(dT)$_{30}$–latex and PCR: isolation of cDNA clones specific to undifferential human enbryonal carcinoma cells", *Nucleic Acids Res.*, vol. 19, No. 25, 1991, pps. 7097–7104.

IntelliGenetics Suite ™, Release 5.4, Advanced Training Manual, Jan. 1993, pps. 1–6, 1–19, 2–9 and 2–14.

Khan et al., "Single pass sequencing and physical and genetic mapping of human brain cDNAs", *Nature Genetics.*, vol. 2, Nov. 1992, pps. 180–185.

Kwoh et al., "Transcription–Based Amplification System and Detection of Amplified Human Immunodeficiency Virus Type 1 with a Bead–Based Sandwich Hybridization Format", *Proc. Natl. Acad. Sci. USA*, vol. 86, No. 4, 1989, pps. 1173–1177.

Landegren et al., "A Ligase–Medicated Gene Detection Technique", *Science*, vol. 241, No. 4869, 1988, pps. 1077–1080.

Mattila et al., "Fidelity of DNA Synthesis by the Thermococcus Litoralis DNS Polymerase—An Extremely Heat Stable Enzyme with Proofreading Activity", *Nucleic Acids Res.*, vol. 19, No. 18, 1991, pp. 4967–4973.

Matsubara et al., "Identification of New Genes by Systematic Analysis of cDNAs and Database Construction", *Curr. Opin. Biotechnol.*, vol. 4, No. 6, 1993, pps. 672–677.

Orita et al., "Detection of polymorphisms of human DNA by gel electrophresis was wingle–strand conformation polymorphisms", *Proc. Natl. Acad. Sci. USA*, vol. 86, Apr. 1989, pps. 2766–2770.

Okubo et al., "Large Scale cDNA Sequencing for Analysis of Quantitative and Qualitative Aspects of Gene Expression Expression", *Nature Genetics*, vol. 2, 1993, pps. 173–179.

PR Newswire, "Gene Logic to Use Affymetrix GeneChip Arrays to Build Gene Expression Database Products", Jan. 11, 1999.

Saiki et al., "Analysis of Enzymatically Amplified Beta–Globin and HLA–DQ Alpha DNA with Allele–Specific Oligonucleotide Probes", *Nature*, vol. 324, No. 3093, 1986, pps. 163–166.

Wu et al., "The Ligation Amplification Reaction (LAR)— Amplicifation of specific DNA Sequences Using Sequential Rounds of Template–Dependent Ligation", *Genomics*, vol. 4, No. 4, 1989, pps. 560–569.

Zhao et al., "High–density cDNA filter analysis: a novel approach for large–scale, quantitative analysis of gene expression", *Gene*, vol. 156, 1995, pps. 207–213.

* cited by examiner

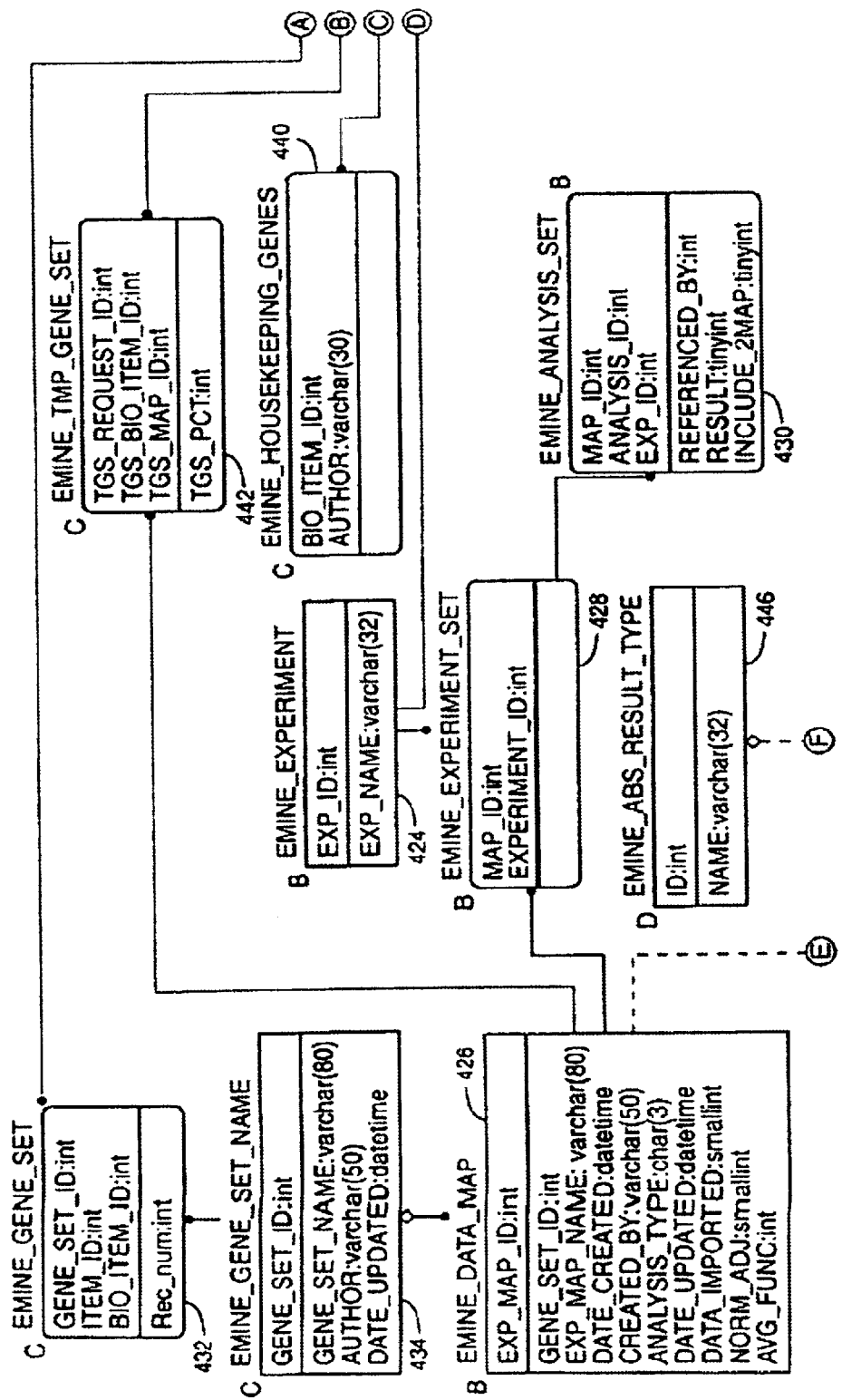
FIG. 4A.1

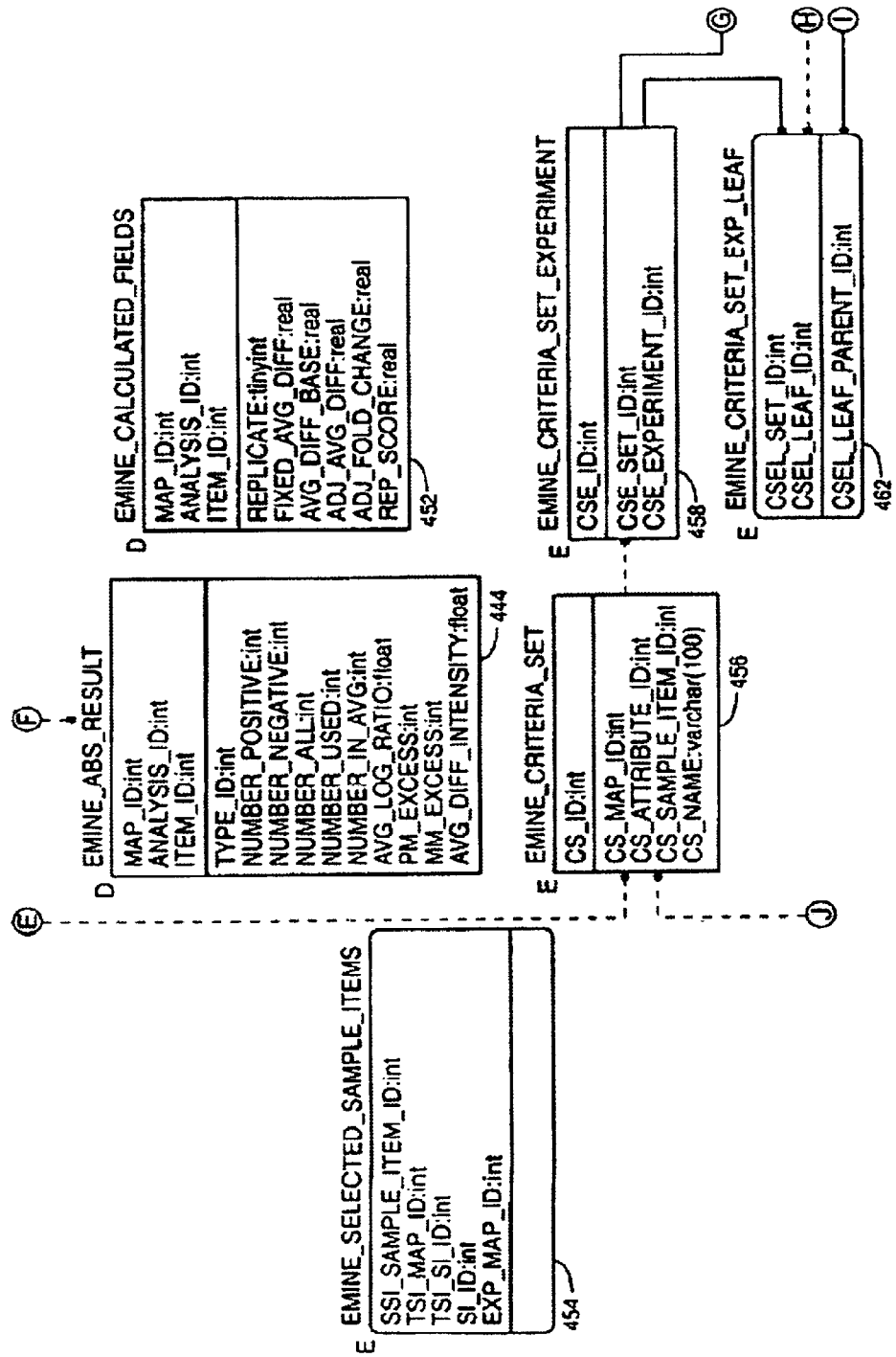
FIG. 4A.2

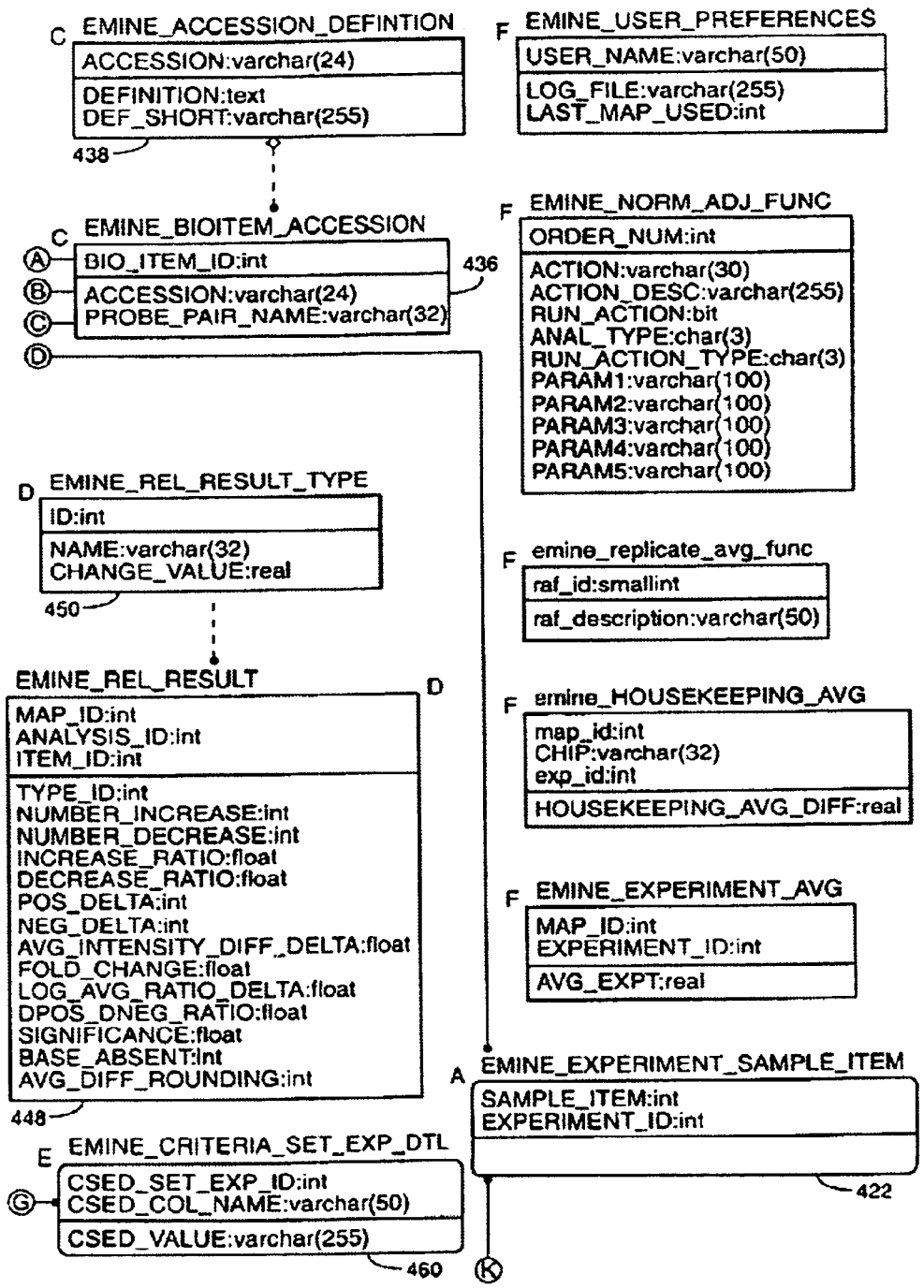
FIG. 4A.3

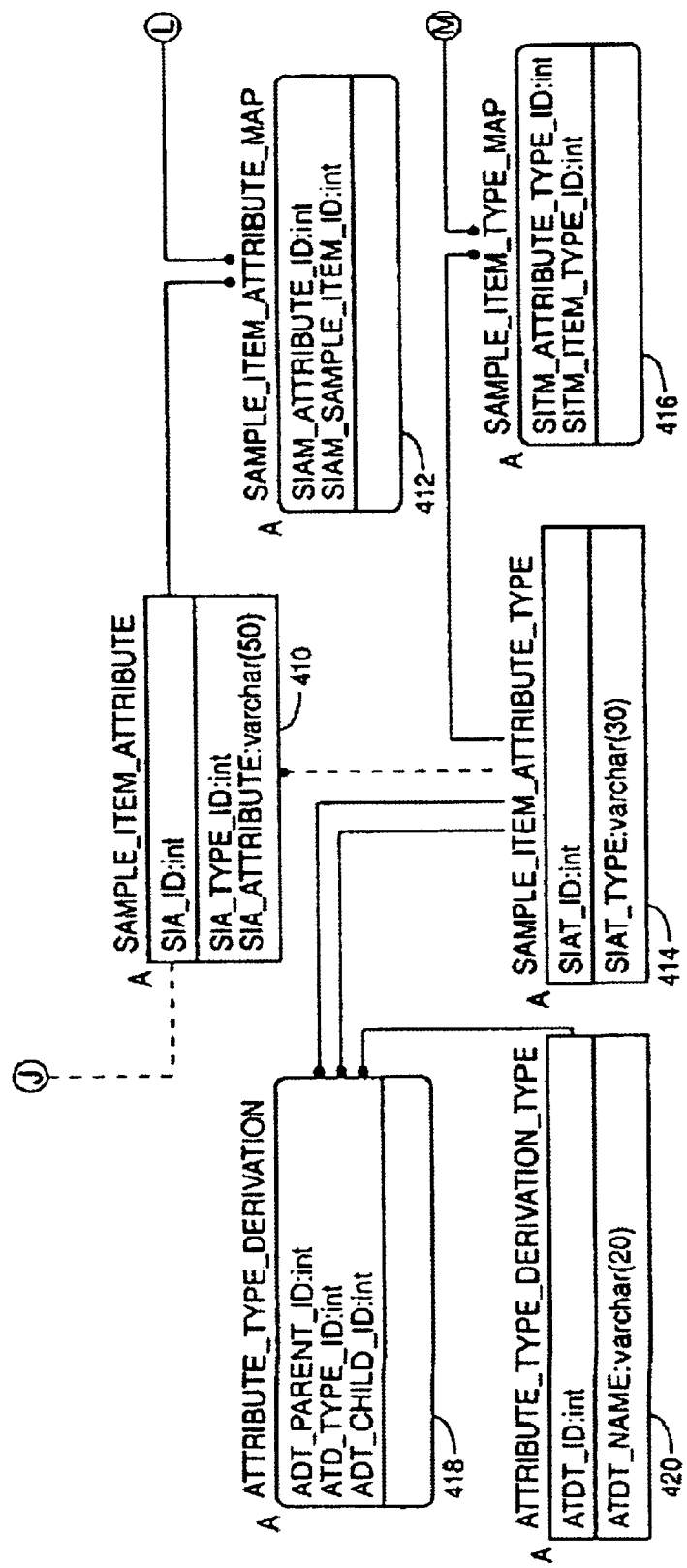
FIG. 4A.4

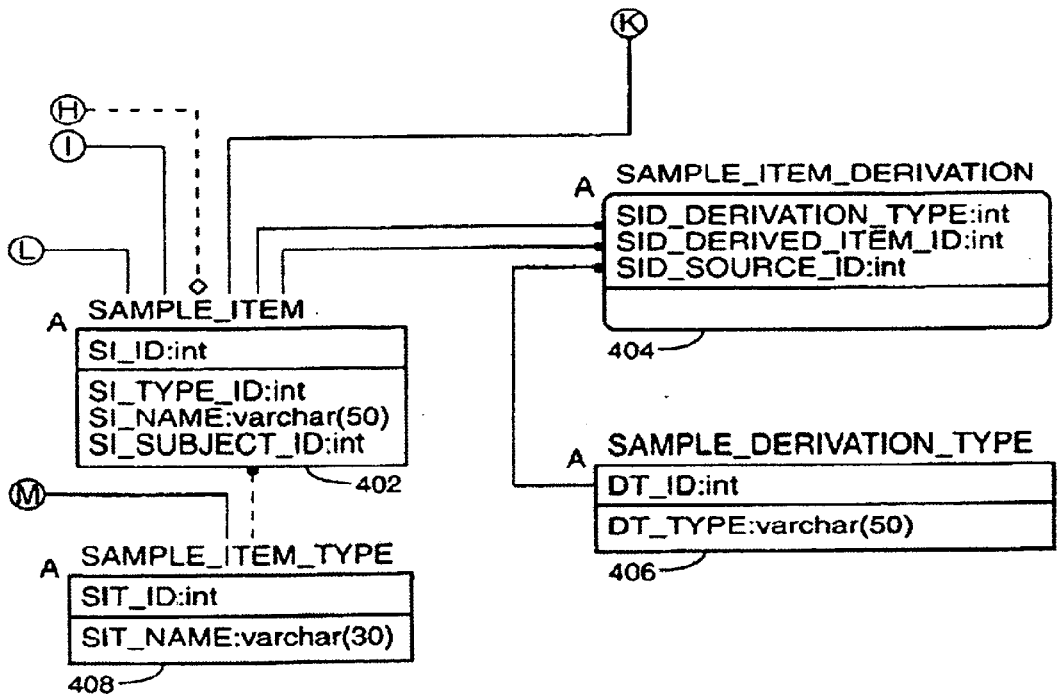
*FIG. 4A.5*
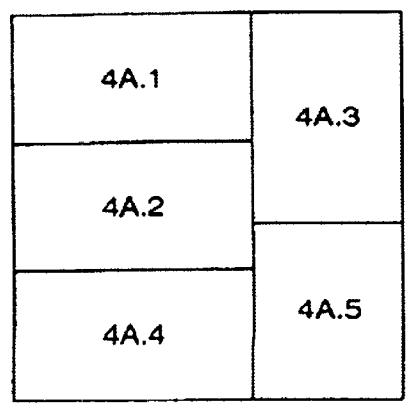
*FIG. 4A*

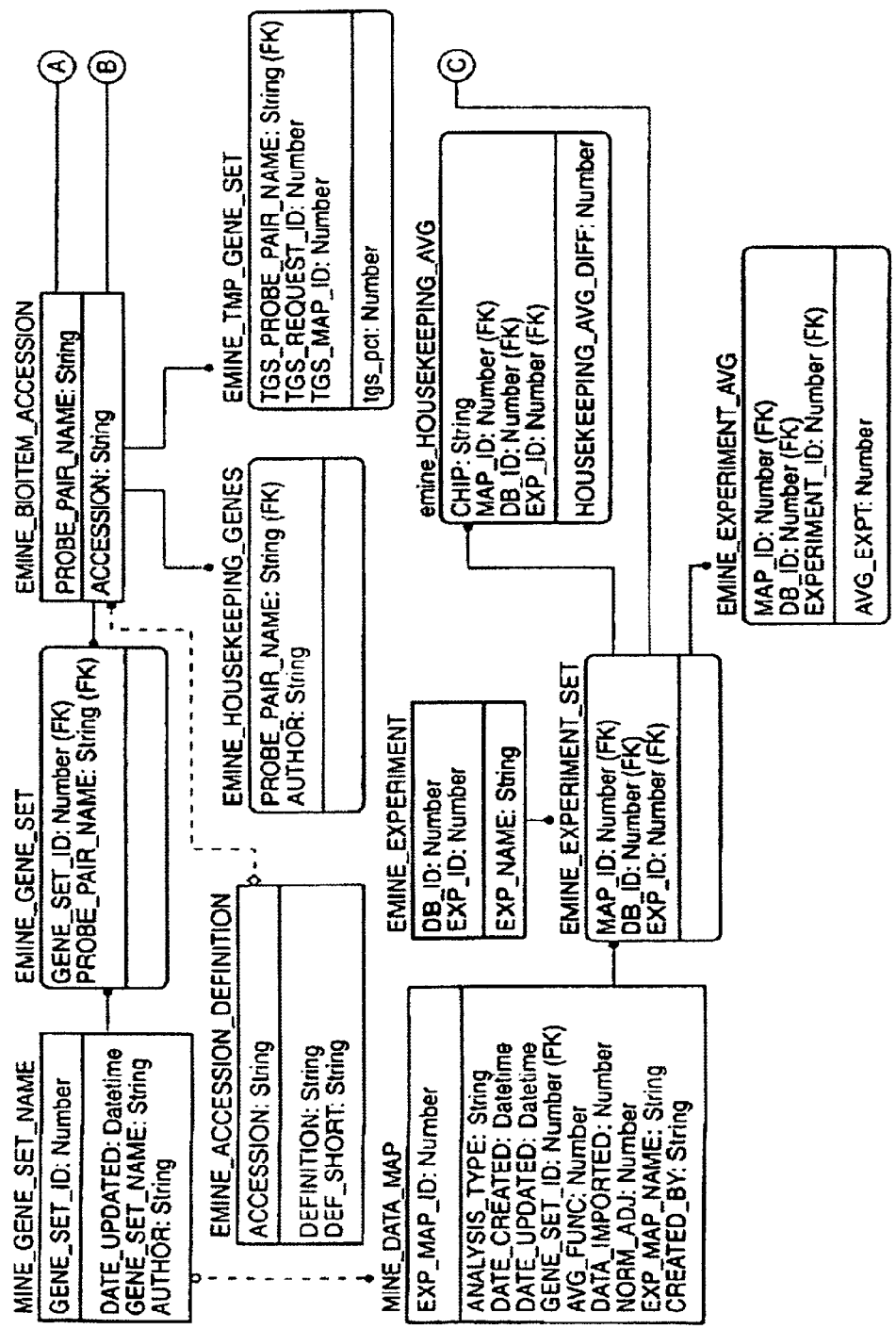
FIG. 4D.1

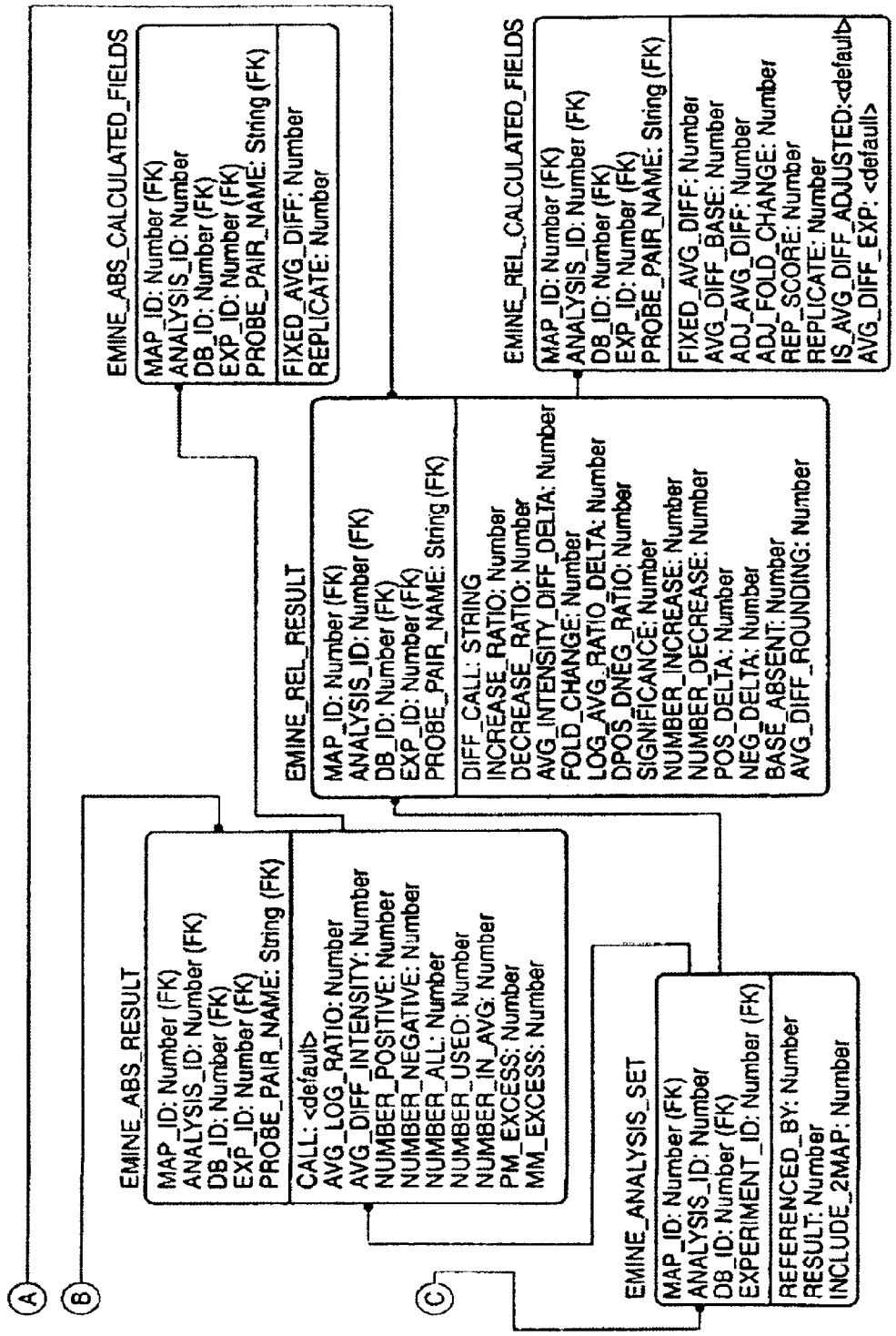
FIG. 4D.2

EMINE_SELECTED_SAMPLE_ITEMS

SSI_MAP_ID
SSI_SAMPLE_ITEM_ID

EMINE_TMP_SAMPLE_ITEM_ID

TSI_MAP_ID
TSI_SI_ID

EMINE_REPLICATE_AVG_FUNC

RAF_ID
RAF_DESCRIPTION

EMINE_NORM_ADJ_FUNC

ORDER_NUM
RUN_ACTION
ANAL_TYPE
RUN_ACTION_TYPE
ACTION
ACTION_DESC
PARAM1
PARAM2
PARAM3
PARAM4
PARAM5

EMINE_USER_PREFERENCES

USER_NAME
UPDATE_BIO_REF
LAST_MAP_USED
LAST_DB_ID
LOG_FILE

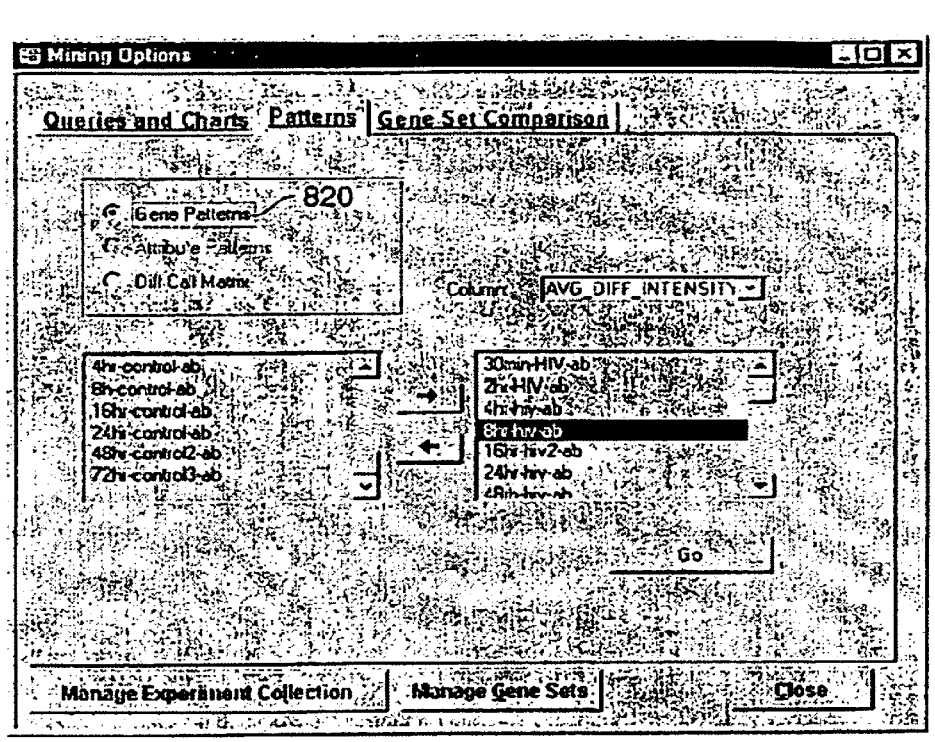
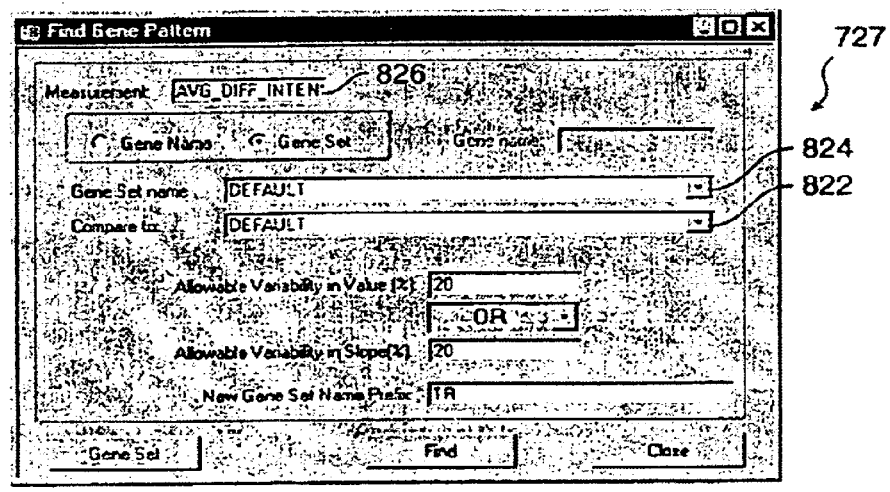
FIG. 7L

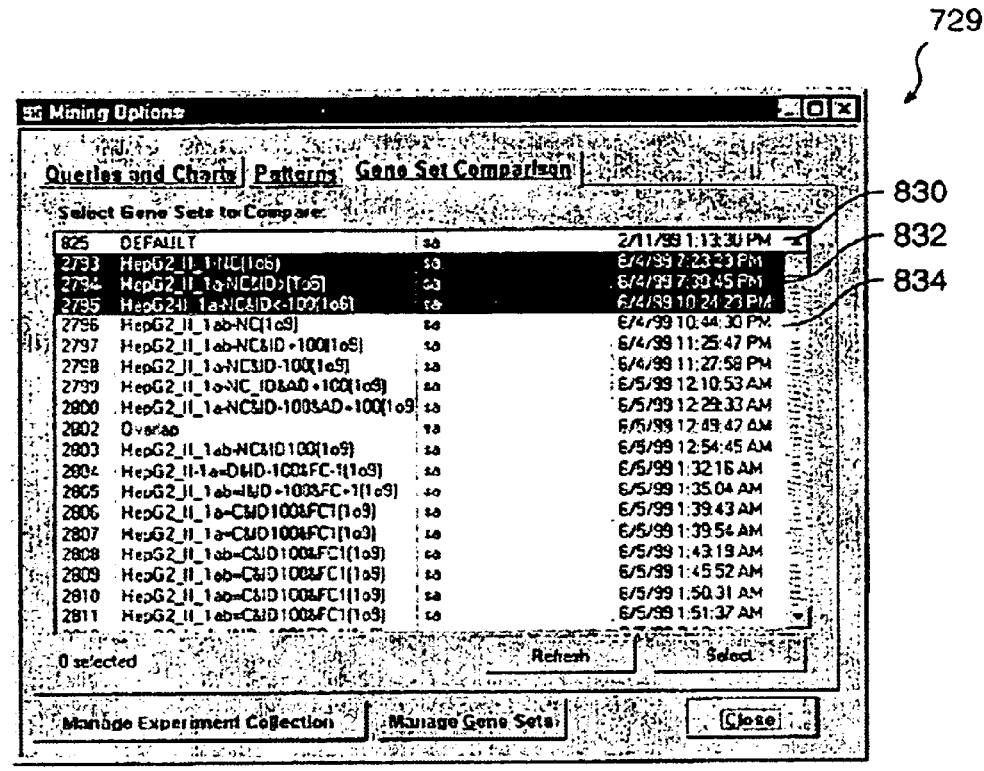
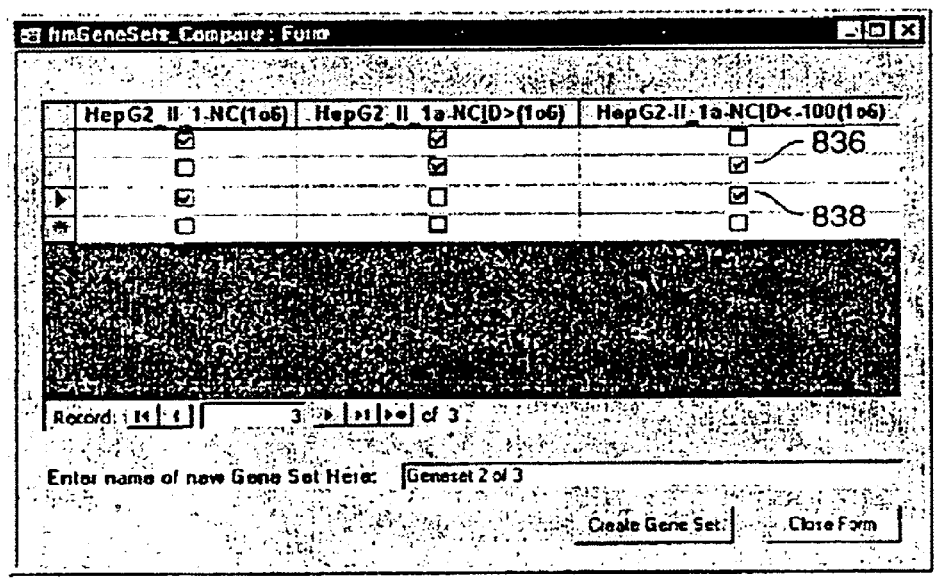
FIG. 7M

| ACCESSION | PROBE_PAIR_NAME | DEFINITION |
|---|---|---|
| 1-Apr | 1-Apr | |
| A28102 | A28102_at | Human GABAa receptor alpha-3 subunit |
| AB000114 | AB000114_at | Human mRNA for osteomodulin, complete cds |
| AB000115 | AB000115_at | Human mRNA, complete cds |
| AB000220 | AB000220_at | Human mRNA for semaphorin E, complete cds |
| AB000381 | AB000381_s_at | Human DNA for GPI-anchored molecule-like protein, complete cds |
| AB000409 | AB000409_at | Human mRNA for MNK1, complete cds |
| AB000410 | AB000410_s_at | Human mRNA for hOGG1 mRNA, complete cds |
| AB000449 | AB000449_at | Human mRNA for VRK1, complete cds |
| AB000450 | AB000450_at | Human mRNA for VRK2, complete cds |
| AB000460 | AB000460_at | Human mRNA, clone RES4-22B, complete cds |
| AB000462 | AB000462_at | Human mRNA for SH3 binding protein, clone RES4-23A, complete cr |

METHOD AND APPARATUS FOR PROVIDING AN EXPRESSION DATA MINING DATABASE

CROSS-REFERENCES TO RELATED APPLICATIONS

This application is a continuation of application Ser. No. 09/354,935, filed Jul. 15, 1999, now U.S. Pat. No. 6,185,561, which claims priority from the following U.S. Provisional Patent Application, the disclosure of which, including all appendices and all attached documents, is incorporated by reference in its entirety for all purposes:

U.S. Provisional Patent Application Ser. No. 60/100,740, David J. Balaban and Elina Khurgin entitled, "METHOD AND APPARATUS FOR PROVIDING AN EXPRESSION DATA MINING DATABASE," filed Sep. 17, 1998.

The subject matter of the present application is related to the subject matter of the following two co-assigned applications filed on Jul. 24, 1998. U.S. patent application Ser. No. 09/122,434, David J. Balaban entitled, GENE EXPRESSION AND EVALUATION SYSTEM, now U.S. Pat. No. 6,308,170 and U.S. patent application Ser. No. 09/122,167, David J. Balaban and Arun Aggarwal entitled, METHOD AND APPARATUS FOR PROVIDING A BIOINFORMATICS DATABASE, now U.S. Pat. No. 6,229,911. The contents of these two applications are herein incorporated by reference in their entirety for all purposes.

BACKGROUND OF THE INVENTION

The present invention relates to computer systems and more particularly to computer systems for mining information about gene expression levels.

Devices and computer systems have been developed for collecting information about gene expression or expressed sequence tags (EST) in large numbers of samples. For example, PCT application WO92/10588, incorporated herein by reference for all purposes, describes techniques for sequence checking nucleic acids and other materials. Probes for performing these operations may be formed in arrays according to the pioneering techniques disclosed in U.S. Pat. Nos. 5,143,854 and 5,571,639, for example. Both of these U.S. Patents are incorporated herein by reference for all purposes.

According to one aspect of the techniques described in these patents, an array of nucleic acid probes is fabricated at known locations on a chip or substrate. A fluorescent label attached to a nucleic acid is then brought into contact with the chip and a scanner generates an image file indicating the locations where the labeled nucleic acids bound to the chip. Based upon the identities of the probes at these locations, information such as the monomer sequence of DNA or RNA can be extracted.

Computer-aided techniques for gene expression monitoring using such arrays of probes have been developed as disclosed in EP Pub. No. 0848067 and PCT publication No. WO 97/10365, the contents of which are herein incorporated by reference. Many diseases are characterized by differences in the degree that various genes are expressed either through changes in the copy number of the genetic DNA or through changes in levels of transcription (e.g., through control of initiation, provision of RNA precursors, RNA processing, etc.) of particular genes. For example, losses and gains of genetic material play an important role in malignant transformation and progression. Furthermore, changes in the expression (transcription) levels of particular genes (e.g., oncogenes or tumor suppressors), serve as signposts for the presence and progression of various cancers.

Information on expression of genes or expressed sequence tags may be collected on a large scale in many ways, including the probe array techniques described above. One of the objectives in collecting this information is the identification of genes or ESTs whose expression is of particular importance. Researchers use such techniques to answer questions such as: 1) Which genes are expressed in cells of a malignant tumor but not expressed in either healthy tissue or tissue treated according to a particular regime? 2) Which genes or ESTs are expressed in particular organs but not in others? 3) Which genes or ESTs are expressed in particular species but not in others?

Collecting vast amounts of expression data from large numbers of samples including many tissue types is useful in answering these questions. However, in order to derive full benefit from the investment made in collecting and storing expression data, techniques enabling one to efficiently mine the data to find items of particular relevance are highly desirable.

SUMMARY OF THE INVENTION

The present invention provides techniques for organizing expression or concentration information in a way that facilitates mining. A database model is provided which may organize information relating to, e.g., sample preparation, expression analysis of experiment results, and intermediate and final results of mining gene expression measurements, gene sets and the like. The model is readily translatable into database languages such as SQL and the like. The database model can scale to permit mining of gene expression measurements collected from large numbers of samples.

According to an embodiment of the present invention, a computer based method for mining a plurality of experiment information is provided. The method includes a variety of steps such as collecting information from experiments and chip designs. The method can include steps of selecting experiments to be mined. Experiment results and other information can be organized by experimental analysis, and the like. A step of defining one or more groupings for the experiments to be mined is also be part of the method. The method also includes a step of selecting based upon the groupings, information about the experiments to be mined to form a plurality of resulting information. This resulting information can include one or more resulting gene sets, and the like. Finally, the method formats the resulting information for viewing by a user. The combination of these steps can provide to the user the ability to access experiment information.

In some embodiments, visualization techniques can be used in conjunction with the steps of the method to enable users to more easily understand the results of the data mining. Further, in some embodiments, a step of recording conclusions about the results of the data mining can also be part of the method.

In another aspect according to the present invention, a method for working with expression information is provided. The method includes a variety of steps such as collecting information about results of experiments. A step of gathering information about samples and information about the experiments, which can comprise an experimental analysis and the like, is also part of the method. The step of adding one or more attributes to the information about the experiments can also be performed. The method then transforms the plurality of results of experiments into a plurality of transformed information. Transformations can include normalizing, de-normalizing, aggregation, scaling, and the like. Steps of mining the plurality of transformed information and visualizing the plurality of transformed information can also be part of the method.

Numerous benefits are achieved by way of the present invention over conventional techniques. Some embodiments according to the present invention can provide better access to genetic experiment information than methods known in the prior art. Embodiments can provide answers to queries such as, "show all genes where the gene expression value is greater than or equal to 100, where at least three genes out of four respond to the query," as well as answers to many other and varied useful queries. Another advantage provided by this approach is that the results of numerous experiments can be mined effectively using visualization techniques and set theory queries.

A further understanding of the nature and advantages of the inventions herein may be realized by reference to the remaining portions of the specification and the attached drawings.

BRIEF DESCRIPTION OF THE DRAWINGS

FIGS. 4A–4F illustrate a database model for maintaining information for the system and method of FIG. 1 in a particular embodiment according to the present invention.

DESCRIPTION OF THE SPECIFIC EMBODIMENTS

One embodiment of the present invention operates in the context of a system for analyzing biological or other materials using arrays that themselves include probes that may be made of biological materials such as RNA or DNA. The VLSIPS™ and GeneChip™ technologies provide methods of making and using very large arrays of polymers, such as nucleic acids, on very small chips. Reference may be had to U.S. Pat. No. 5,143,854 and PCT Patent Publication Nos. WO 90/15070 and 92/10092, each of which is hereby incorporated by reference in its entirety for all purposes. Nucleic acid probes on the chip are used to detect complementary nucleic acid sequences in a sample nucleic acid of interest (the "target" nucleic acid).

It should be understood that the probes need not be nucleic acid probes but may also be other polymers such as peptides. Peptide probes may be used to detect the concentration of peptides, polypeptides, or polymers in a sample. The probes should be carefully selected to have bonding affinity to the compound whose concentration they are to be used to measure.

Figure 1:
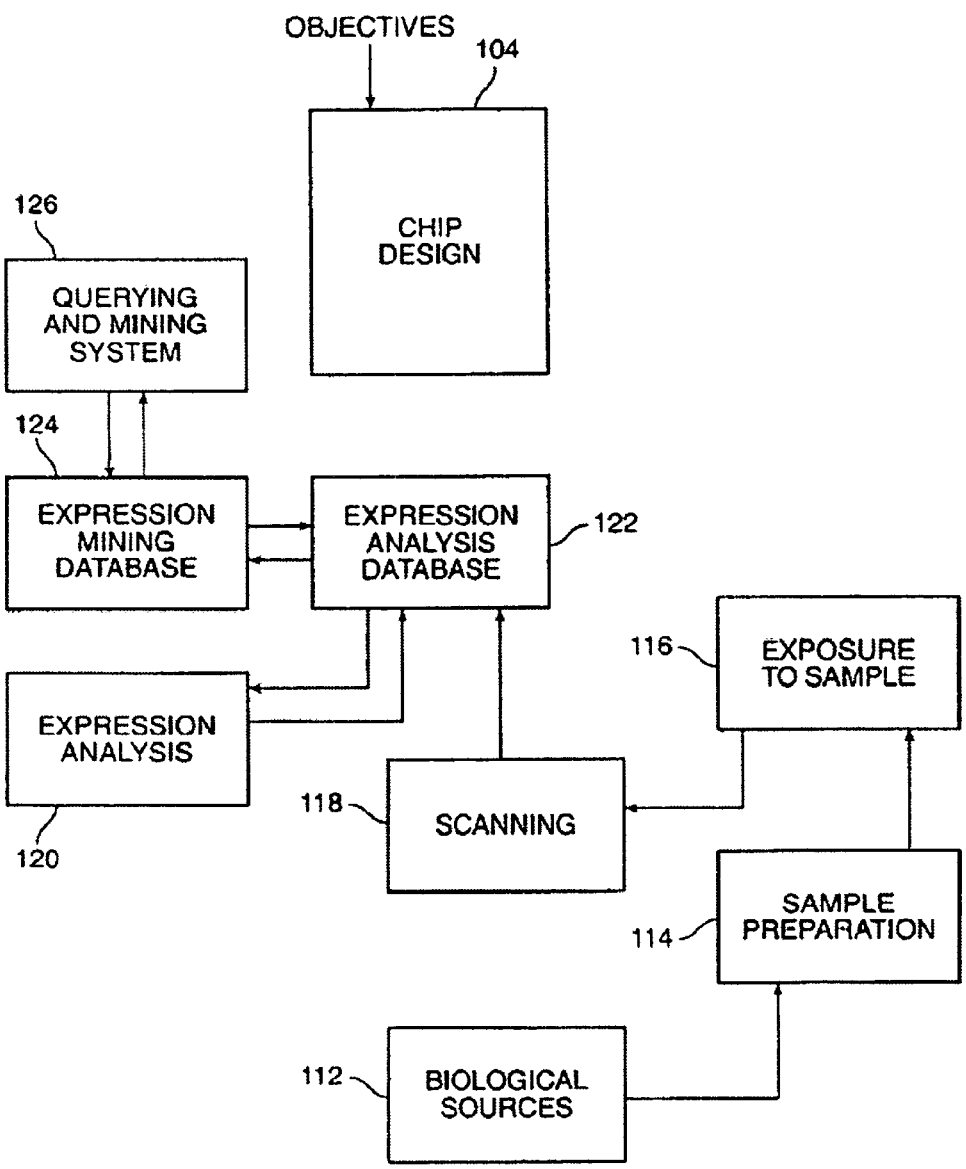
FIG. 1 illustrates a representative system and process for forming and analyzing arrays of biological materials such as DNA or RNA in a particular embodiment according to the present invention.

FIG. 1 illustrates a simplified diagram of a representative example system 100 for forming and analyzing arrays of biological materials such as RNA or DNA. This diagram is merely an illustration and should not limit the scope of the claims herein. One of ordinary skill in the art would recognize other variations, modifications, and alternatives. A chip design system 104 is used to design arrays of polymers such as biological polymers such as RNA or DNA. Chip design system 104 may be, for example, an appropriately programmed Sun Workstation or personal computer or workstation, such as an IBM PC equivalent, and the like. Chip design system 104 obtains inputs from a user regarding chip design objectives including characteristics of genes of interest, and other inputs regarding the desired features of the array. Optionally, chip design system 104 may obtain information regarding a specific genetic sequence of interest from bioinformatics database 102 or from external databases such as GenBank. The output of chip design system 104 is a set of chip design computer files in the form of, for example, a switch matrix, as described in PCT application WO 92/10092, and other associated computer files. Systems for designing chips for sequencing, sequence checking and expression analysis are disclosed in U.S. Pat. No. 5,571,639 and in PCT application WO 97/10365, the entire contents of which are herein incorporated by reference for all purposes.

The chip design files are input to a mask design system (not shown) that designs the lithographic masks used in the fabrication of arrays of molecules such as DNA. The mask design system designs the lithographic masks used in the fabrication of probe arrays. The mask design system generates mask design files that are then used by a mask construction system (not shown) to construct masks or other synthesis patterns such as chrome-on-glass masks for use in the fabrication of polymer arrays.

The masks are used in a synthesis system (not shown). The synthesis system includes the necessary hardware and software used to fabricate arrays of polymers on a substrate or chip. The synthesis system includes a light source and a chemical flow cell on which the substrate or chip is placed. A mask is placed between the light source and the substrate/chip, and the two are translated relative to each other at appropriate times for deprotection of selected regions of the chip. Selected chemical reagents are directed through the flow cell for coupling to deprotected regions, as well as for washing and other operations. The substrates fabricated by the synthesis system are optionally diced into smaller chips. The output of the synthesis system is a chip ready for application of a target sample. Information about the mask design, mask construction, and probe array synthesis systems is presented by way of background.

A biological source 112 is, for example, tissue from a plant or animal. Various processing steps are applied to material from biological source 112 by a sample preparation system 114. These steps may include isolation of mRNA, precipitation of the mRNA to increase concentration. The result of the various processing steps is a target sample ready for application to the chips produced by the synthesis system 110. Sample preparation methods for expression analysis are discussed in detail in WO97/10365.

The prepared samples include monomer nucleotide sequences such as RNA or DNA. When the sample is applied to the chip by a sample exposure system 116, the nucleotides may or may not bond to the probes. The nucleotides have been tagged with fluorescein labels to determine which probes have bonded to nucleotide sequences from the sample. The prepared samples will be placed in a scanning system 118. Scanning system 118 includes a detection device such as a confocal microscope or CCD (charge-coupled device) that is used to detect the location where labeled receptors have bound to the substrate. The output of scanning system 118 is an image file(s) indicating, in the case of fluorescein labeled receptor, the fluorescence intensity (photon counts or other related measurements, such as voltage) as a function of position on the substrate. Since higher photon counts will be observed where the labeled receptor has bound more strongly to the array of polymers, and since the monomer sequence of the polymers on the substrate is known as a function of position, it becomes possible to determine the sequence(s) of polymer(s) on the substrate that are complementary to the receptor.

The image files and the design of the chips are input to an analysis system 120 that, e.g., calls base sequences, or determines expression levels of genes or expressed sequence tags. The expression level of a gene or EST is herein understood to be the concentration within a sample of mRNA or protein that would result from the transcription of the gene or EST. Such analysis techniques are disclosed in WO97/10365 and U.S. application Ser. No. 08/531,137, the entire contents of which are herein incorporated by reference for all purposes.

An expression analysis database 122 maintains information used to analyze expression and the results of expression analysis. Contents of expression analysis database 122 may include tables listing analyses performed, analysis results, experiments performed, sample preparation protocols and parameters of these protocols, chip designs, etc. Details of one embodiment of expression analysis database 122 are described in U.S. patent application Ser. No. 09/122,167, entitled METHOD AND APPARATUS FOR PROVIDING A BIOINFORMATICS DATABASE, filed on Jul. 24, 1998, the entire contents of which are incorporated herein by reference for all purposes.

One or more instantiations of expression analysis database 122 may contain information concerning the expression of many genes or ESTs as collected from many different tissue samples. It would be useful to use this information to investigate questions such as, e.g., 1) which genes or ESTs are upregulated (expressed more) in diseased tissue and downregulated (expressed less) in disease tissue, 2) how does gene expression vary among organs and tissue types within a species, 3) how does gene expression vary among species which share common genes, 4) how does gene expression respond to various disease treatment regimes, 5) how does gene expression vary with progression of disease, etc.

To facilitate investigations of this kind, an expression mining database 124 is provided. Expression mining database 124 may include duplicate representations of data in expression analysis database. Expression mining database 124 may also include various tables to facilitate mining operations conducted by a user who operates a querying and mining system 126. Querying and mining system 126 includes a user interface that permits an operator to make queries to investigate expression of genes and ESTs and answer the types of questions identified above. An example of a querying and mining system is described in U.S. patent application Ser. No. 09/122,434, entitled GENE EXPRESSION AND EVALUATION SYSTEM, filed Jul. 24, 1998, the entire contents of which are incorporated herein by reference for all purposes.

Chip design system 104, analysis system 120 and control portions of exposure system 116, sample preparation system 114, and scanning system 118 may be appropriately programmed computers such as a Sun workstation or IBM-compatible PC. An independent computer for each system may perform the computer-implemented functions of these systems or one computer may combine the computerized functions of two or more systems. One or more computers may maintain expression analysis database 122, expression mining database 124, and querying and mining system 126 independent of the computers operating the systems of FIG. 1.

Figure 2A:
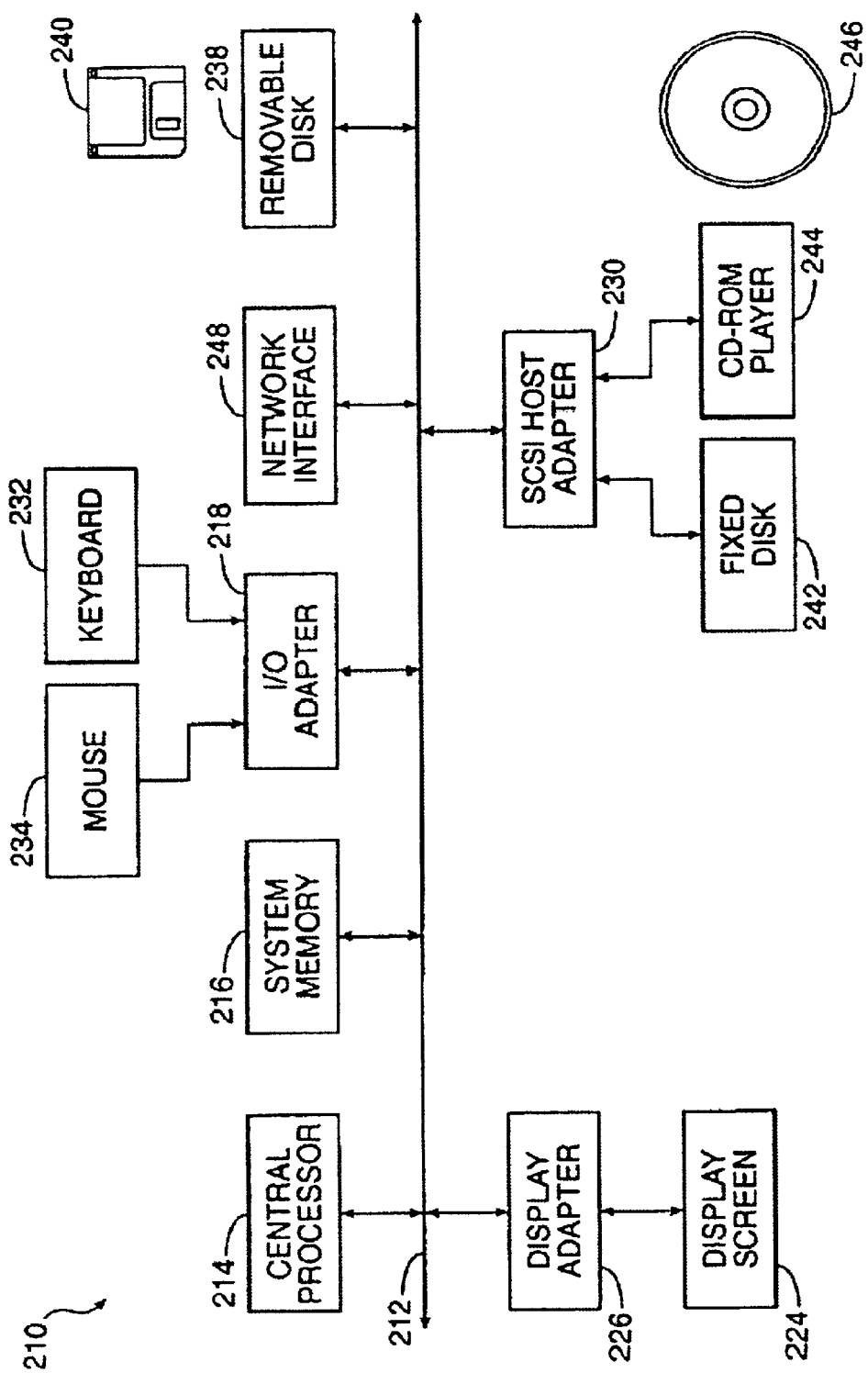
FIG. 2A illustrates a computer system suitable for use in conjunction with the representative system of FIG. 1.

FIG. 2A depicts a simplified block diagram of a representative host computer system 10 in a particular embodiment according to the present invention. This diagram is merely an illustration and should not limit the scope of the claims herein. One of ordinary skill in the art would recognize other variations, modifications, and alternatives. Host computer system 210 includes a bus 212 which interconnects major subsystems such as a central processor 214, a system memory 216 (typically RAM), an input/output (I/O) adapter 218, an external device such as a display screen 224 via a display adapter 226, a keyboard 232 and a mouse 234 via an I/O adapter 218, a SCSI host adapter 236, and a removable disk drive 238 operative to receive a removable disk 240. SCSI host adapter 236 may act as a storage interface to a fixed disk drive 242 or a CDROM player 244 operative to receive a CD-ROM 246. Fixed disk 244 may be a part of host computer system 210 or may be separate and accessed through other interface systems. A network interface 248 may provide a direct connection to a remote server via a telephone link or to the Internet. Network interface 248 may also connect to a local area network (LAN) or other network interconnecting many computer systems. Many other devices or subsystems (not shown) may be connected in a similar manner.

Also, it is not necessary for all of the devices shown in FIG. 2A to be present to practice the present invention, as discussed below. The devices and subsystems may be interconnected in different ways from that shown in FIG. 2A. The operation of a computer system such as that shown in FIG. 2A is readily known in the art and is not discussed in detail in this application. Code to implement the present invention, may be operably disposed or stored in computer-readable storage media such as system memory 216, fixed disk 242, CD-ROM 246, or removable disk 240.

Figure 2B:
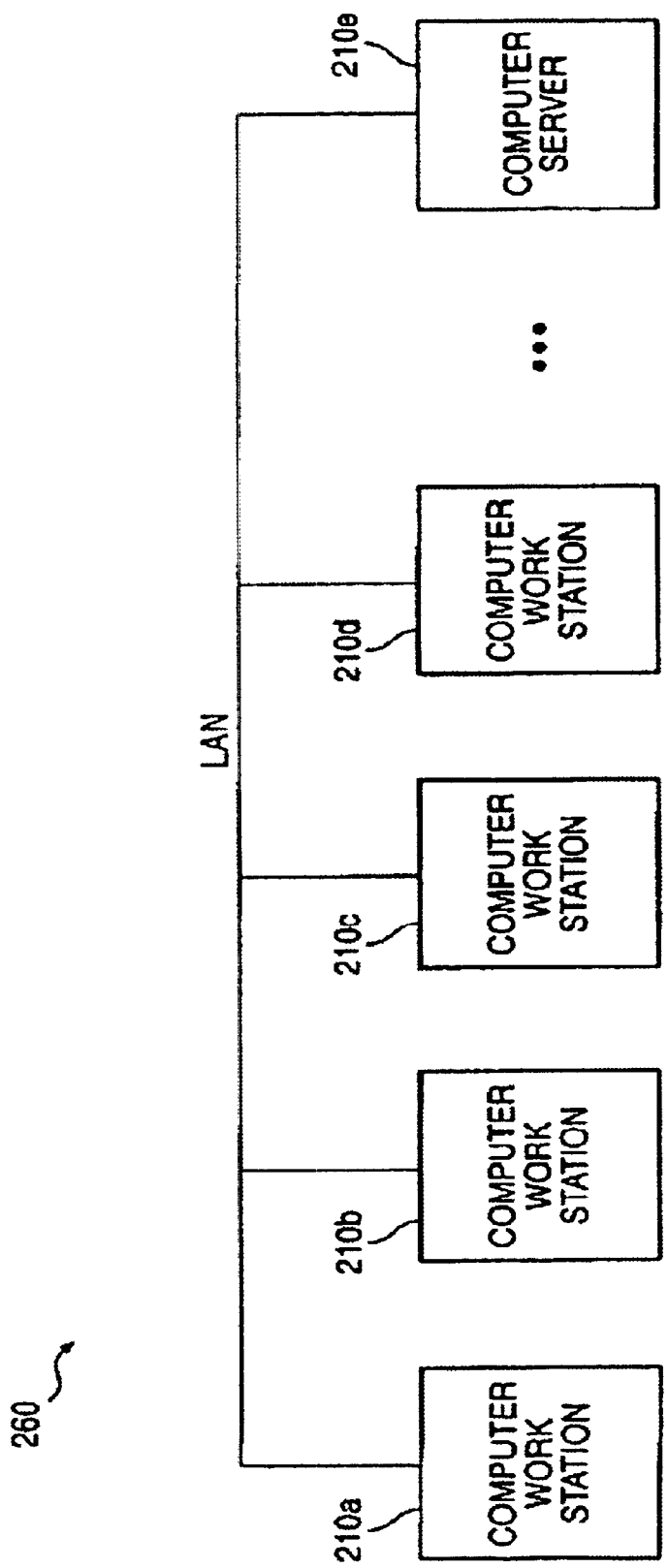
FIG. 2B illustrates a computer network suitable for use in conjunction with the representative system of FIG. 1.

FIG. 2B depicts a simplified diagram of a network 260 interconnecting multiple computer systems 210a–210e. This diagram is merely an illustration and should not limit the scope of the claims herein. One of ordinary skill in the art would recognize other variations, modifications, and alternatives. Network 260 may be a local area network (LAN), wide area network (WAN), etc. Bioinformatics database 102 and the computer-related operations of the other elements of FIG. 2B may be divided amongst computer systems 210 in any way with network 260 being used to communicate information among the various computers. Portable storage media such as removable disks may be used to carry information between computers instead of network 260.

The contents and structure of expression mining database 124 in a particular representative example embodiment according to the present invention will now be described. Expression mining database 124 is preferably a multidimensional relational database with a complex internal structure. However, other types of databases can also be used in select embodiments without departing from the scope of the present invention. The structure and contents of expression mining database 124 will be described with reference to a model that describes the contents of tables of the database as well as interrelationships among the tables. A visual depiction of this model will be an Entity Relationship Diagram (ERD) which includes entities, relationships, and attributes. A detailed discussion of ERDs is found in "ERwin version 3.5.2 Methods Guide" available from Platinum Technologies, Inc., the contents of which are herein incorporated by reference for all purposes. Those of skill in the art will appreciate that automated tools such as ERwin and Developer 2000 available from Oracle will convert the ERD from FIG. 4A directly into executable code such as SQL code for creating and operating the database.

Figure 3:
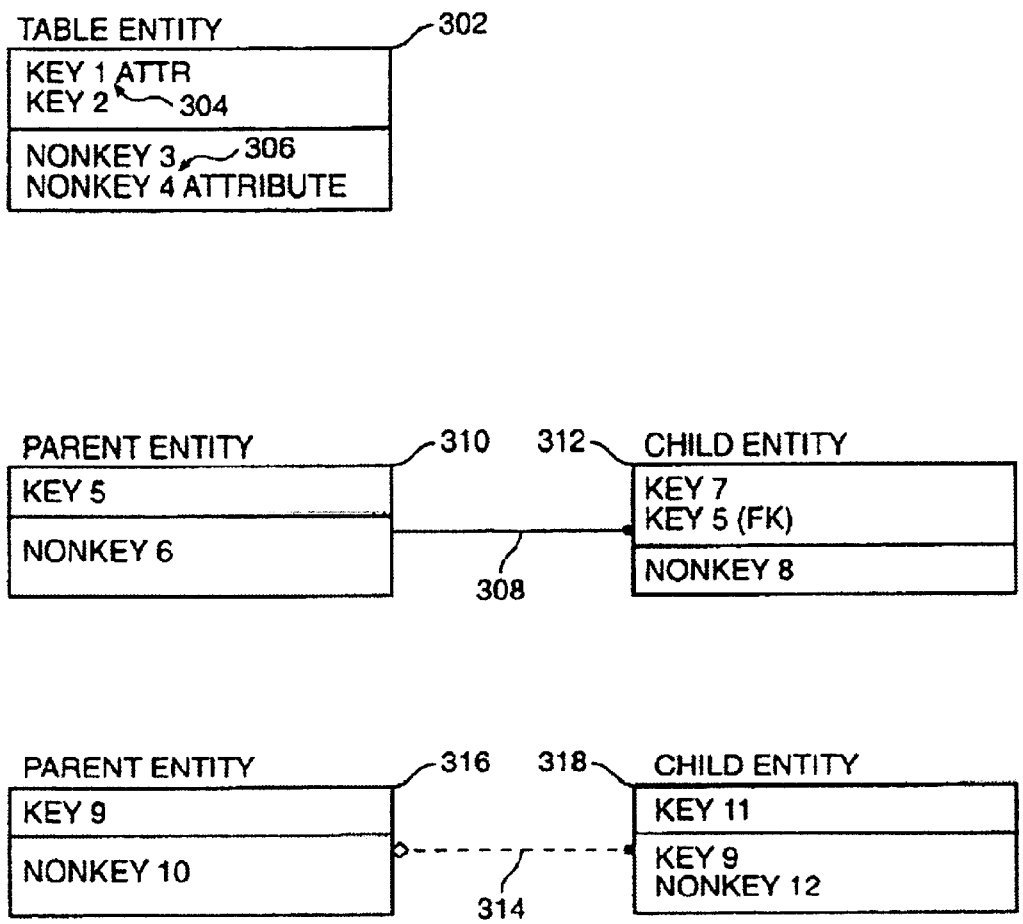
FIG. 3 illustrates an entity relationship diagram for interpreting a database model.

FIG. 3 illustrates a key to ERDs that will be used to describe the contents of chip design database 102. FIG. 3 is merely an illustration and should not limit the scope of the claims herein. One of ordinary skill in the art would recognize other variations, modifications, and alternatives. A representative table 302 includes one or more key attributes 304 and one or more non-key attributes 306. Representative table 302 includes one or more records where each record includes fields corresponding to the listed attributes. The contents of the key fields taken together identify an individual record. In the ERD, each table is represented by a rectangle divided by a horizontal line. The fields or attributes above the line are key while the fields or attributes below the line are non-key attributes. An identifying relationship 308 signifies that the key attribute of a parent table 310 is also a part of a composite key attribute of a child table 312. A nonidentifying relationship 314 signifies that the key attribute of a parent table 316 is also a non-key attribute of a child table 318. Foreign keys, denoted by (FK), comprise attributes of one table that are either a key or a part of a composite of another table. For both the non-identifying and the identifying relationship, one record in the parent table corresponds to one or more records in the child table.

Figure 4B:
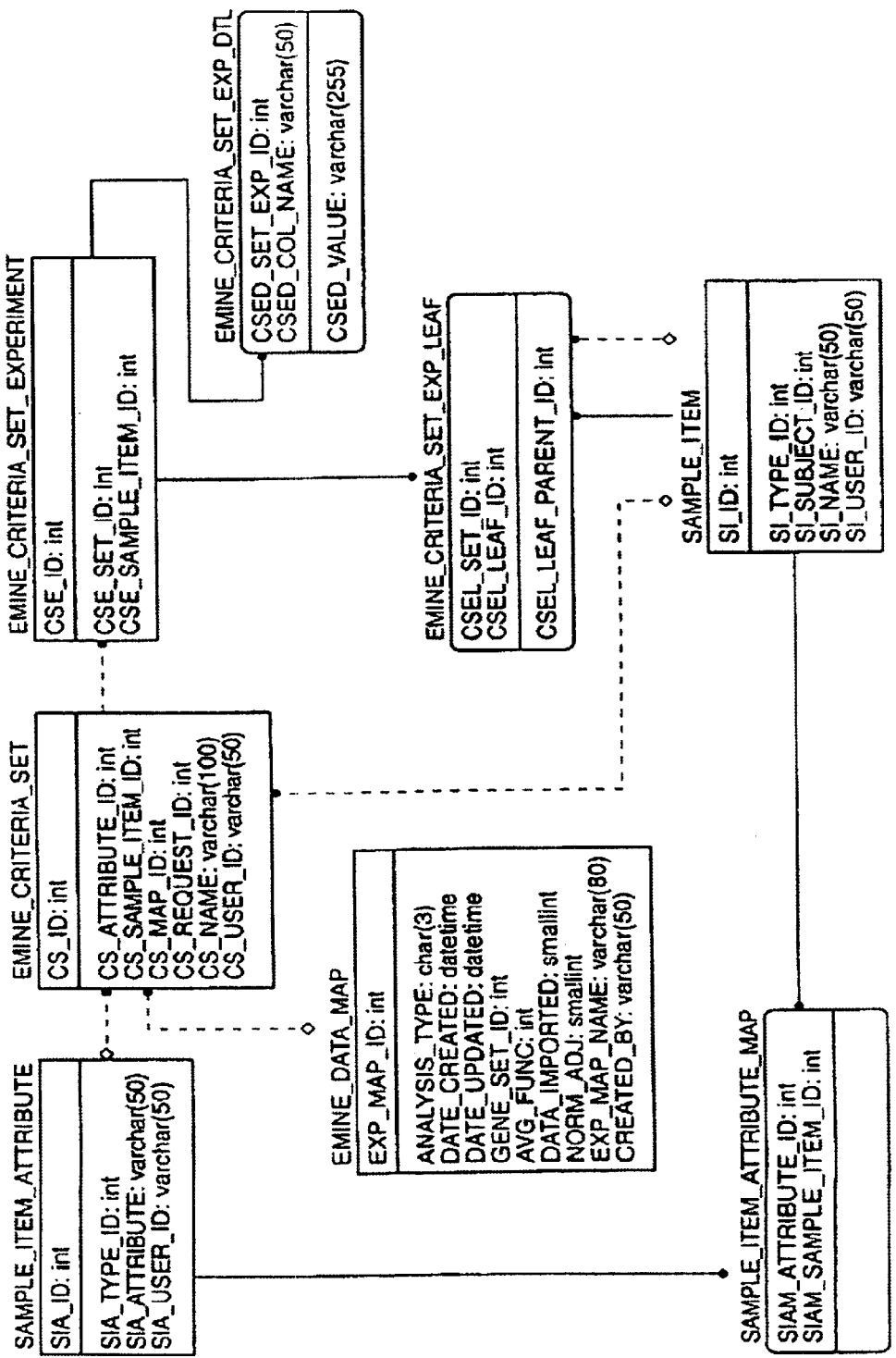
Figure 4C:
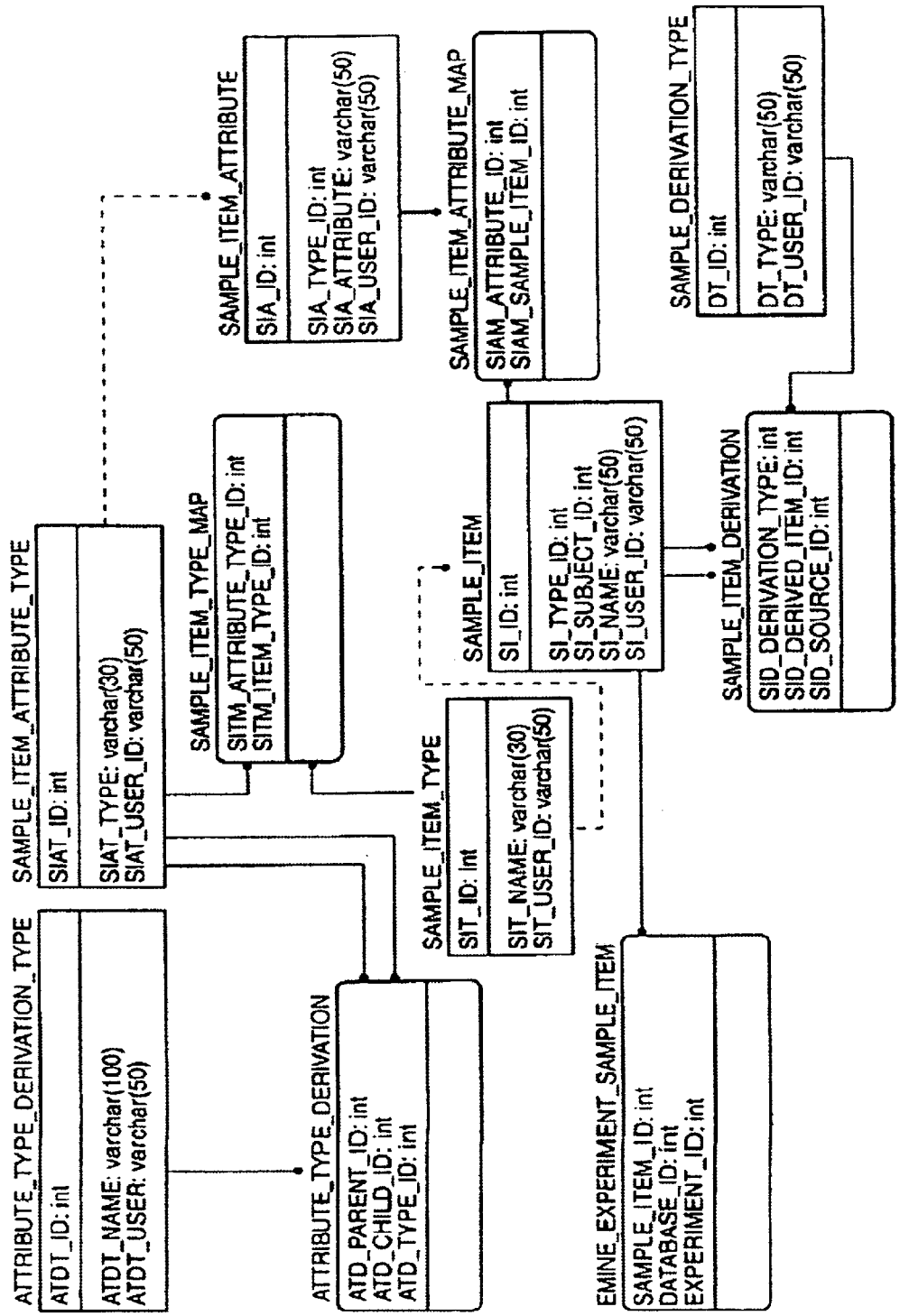
Figure 4F:
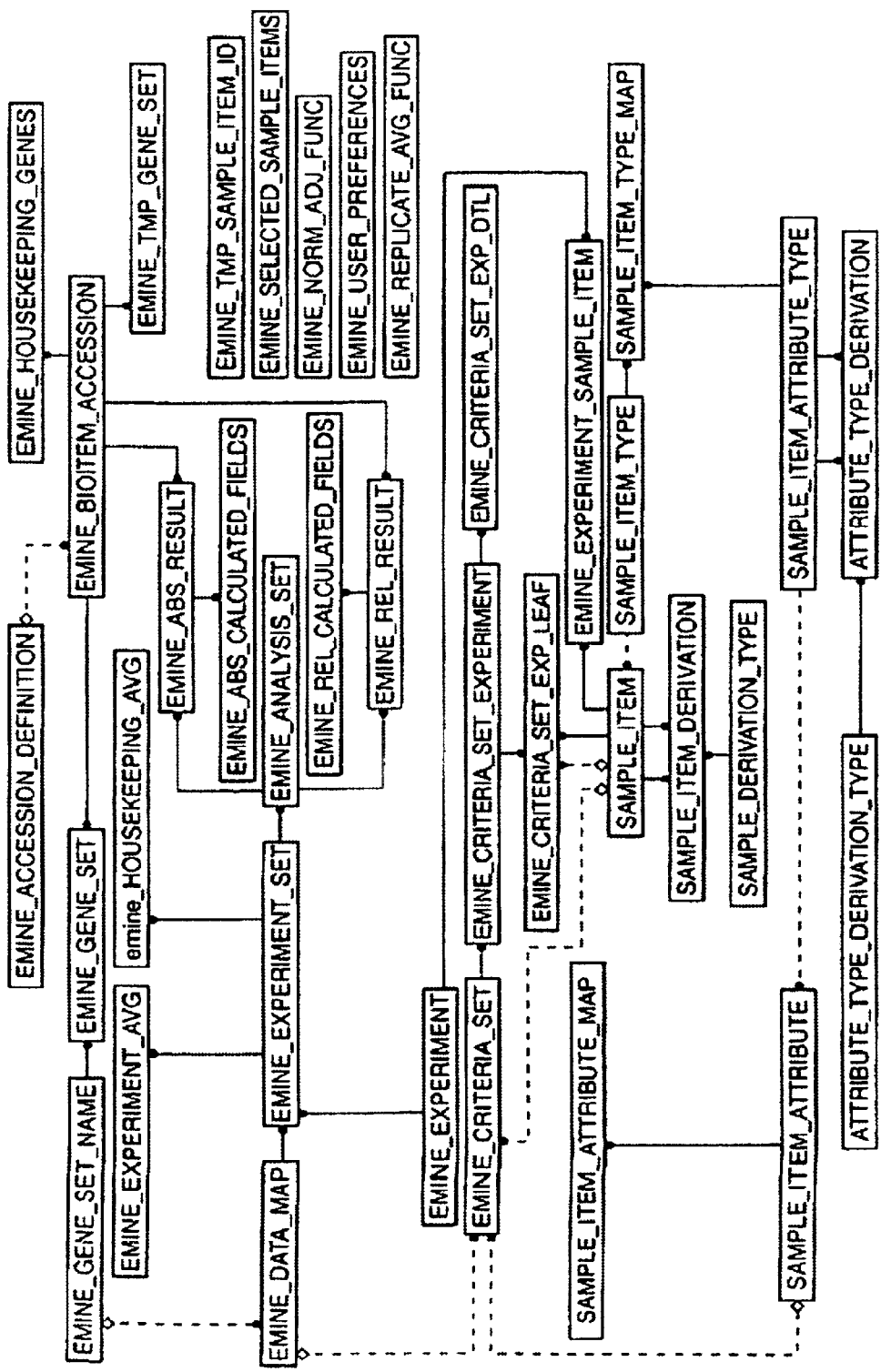

FIG. 4A illustrates a simplified entity relationship diagram (ERD) of elements of expression mining database 124 in a particular embodiment according to the present invention. FIG. 4A is merely an illustration and should not limit the scope of the claims herein. One of ordinary skill in the art would recognize other variations, modifications, and alternatives. Rectangles in FIG. 4A correspond to tables in expression mining database 124. For each rectangle, the title of the table is listed above the rectangle. Within each rectangle, columns of the table are listed. Above a horizontal line within each rectangle are listed key columns, columns whose contents are used to identify individual records in the table. Below this horizontal line are the names of non-key attributes. The lines between the rectangles identify the relationships between records of one table and records of another table. First, the relationships among the various tables will be described. Then, the contents of each table will be discussed in detail.

In operation, expression mining database 124 is updated during mining operations. Certain tables are updated by importation and transformation from expression analysis database 122. Certain other tables may be updated as an operator of querying and mining system 126 defines a query operation.

It can be useful to identify genes or ESTs whose expression varies in some way depending on one or more tissue attributes. Therefore, it is necessary for querying and mining system 126 to have awareness of tissue attributes associated with expression analysis results. One or more analysis results are typically associated with what is herein referred to as "leaf target samples."

In order to provide a more easily understood explanation of the workings of the present invention, the relationship between "leaf target samples" and tissue attributes will first be discussed. A "raw sample" represents a piece of extracted tissue. Before further processing, a single raw sample may be cleaved into multiple raw samples. The raw samples are the input to sample preparation system 114. For each raw sample, sample preparation system 114 prepares a so-called "target" which is a fluid including mRNA or other expression indicator. A "target" may be split into multiple "replicates" and replicates may be pooled to form another target. The individual "targets" that are applied to chips are the leaf target samples. Each application of a "leaf target sample" to a chip represents an experiment. In a presently preferable embodiment, expression analyses can be conducted on experiment data according to one or more selectable criteria to produce experimental analysis result data.

The tables of expression mining database 124 that relate to samples and attributes are identified in FIG. 4A by the letter "A." Leaf target samples, raw samples, replicates, targets, etc. are listed in a sample item table 402. A sample item derivation table 404 lists transformations from one sample item to another. Sample item derivation table lists, e.g., splitting, pooling, and cleaving operations, transformations from raw samples to targets and analyses applied. A sample derivation type table 406 lists the various types of transformation. The various sample item types themselves, e.g., target, replicate, raw sample, leaf target sample, analyses and the like, are listed in a sample item type table 408. Listing the sample derivation types and sample item types allows easy reprogramming to accommodate changes in sample processing procedures.

Associated with samples are attributes. Some of the attributes are strings or values identifying concentrations, sample preparation dates, expiration dates, and the like. Other attributes identify characteristics that are highly useful in searching for genes or ESTs of interest such as the disease state of tissue, the organ, or species from which a sample is extracted. Attributes are listed in a sample item attribute table 410. A sample item attribute map table 412 implements a many-to-many relationship between sample item attribute table 410 and a sample item table 402. A sample may have more than one attribute, and an attribute can describe more than one sample item.

Each attribute has an associated attribute type listed in a sample item attribute type table 414 and an associated value for the attribute. Examples of attribute types are "concentration," "preparation date," "expiration date," etc. Another example of an attribute type would be "specimen type" where possible values would correspond to "tissue," "organ culture," "purified cells," "primary cell culture," "established cell line," and the like. Another example might be "ethnic group" where different values may correspond to "East Asian," Native American," for example.

Many attribute types may be understood to derived from other attribute types. For example, the attribute type "ethnic group" may derived from an attribute type "human" which is in turn derived from an attribute "species." Some attribute types have no associated attributes but rather define levels of categorization. The derivations relating a "parent" attribute type to a "child" attribute type are listed in an attribute type derivation type table 418. Any attribute type may have one or more parents or children. Different types of derivation are listed in an attribute type derivation type table 420. One representative attribute type derivation type is category-subcategory where the parent type represents a category and the child type represents the subcategory. The availability of derivation relationships among attribute types greatly facilitate the formulation of useful queries to expression mining database 124, allowing the user to readily identify attribute types of interest.

Tables related to information about experiments are denoted in FIG. 4A with the letter "B." An experiment table 424 lists experiments whose results are available for querying. A data map table 426 lists entries corresponding to sets of genes or ESTs to be investigated. Each set corresponds to a collection of experiments performed to investigate the genes in the set. An experiment set table 428 lists associations between experiments and entries in data map table 426 and thus defines the collection of experiments corresponding to each gene set. An analysis set table 430 defines sets of analyses that have been performed corresponding to each gene set. Each entry defines an association between an analysis, an experiment and an entry in data map table 426.

Tables related to information about genes are denoted in FIG. 4A with the letter "C." A gene set table 432 defines membership in all sets of genes that have defined by users to prepare for querying and mining operations or have been otherwise defined. A gene set name table 434 lists names for the gene sets. Genes belonging to gene sets are listed in a bio-item accession table 436. Each entry in bio-item accession table 436 identifies an accession number in a bio-item database. Definitions for accession numbers are stored in an accession definition table 438. A housekeeping genes table 440 lists genes with known expression level that are used to calibrate the expression monitoring process.

Tables related to analysis information are denoted with the letter "D." Absolute expression analysis results are stored in an absolute result table 444. Each entry in absolute result table 444 references an absolute result type. Different absolute result types may include e.g., present, marginal, absent, and unknown, indicating an estimate of the expression level of a given gene or EST. The various relative absolute result types are listed in an absolute result type table 446. Relative analysis results are stored in a relative analysis result table 448. Each entry in relative analysis result table 448 references a relative result type listed in a relative result type table 450. Relative analyses compare expression of a gene in two experiments. Different relative result types may include e.g., increased, no change, decreased, and unknown, all describing the change of expression. Tables 448 and 450 are imported from expression analysis database 122 and are read-only from the viewpoint of querying and mining system 126.

Querying and mining system 126 also performs various expression analysis operations. Results of these calculations are maintained in a calculated fields table 452.

Tables related to mining and querying operations are denoted with a letter "E." At any one time, a user considers data from a collection of experiments. A list of the sample items which were used for these experiments is stored in a selected sample item table 454. Selected sample item table 454 is typically much smaller than sample item table 402, which can make query operations faster.

Each entry in a criteria set table 456 identifies a set of criteria used to query a group selected by sample item or by attribute. Each entry in a criteria set experiment table 458 identifies a set of criteria applied to gene or EST expression levels of a particular sample item belonging to a group identified by reference to criteria set table 456. A criteria set experiment detail table 460 includes entries identifying values to be applied as criteria.

A user of querying and mining system 126 does not have access to information about leaf target samples but rather only about their "parents." The expression data can be recorded concerning the leaf target samples. Entries in criteria set experiment table 458 can be associated with sample items in sample item table 458 and leaf target samples corresponding to these sample items by means of a criteria set experiment leaf table 462.

Various other tables can be included in embodiments according to the present invention and are denoted with a letter "F." A user preferences table 464 stores references to user preference files that record the preferences of individual users of querying and mining system 126. Users may wish to store functions used for normalization of expression data for later use. A normalization adjustment function table 466 lists information about normalization and other transformation functions. Users may wish to store functions used to average expression data collected from related replicates. Descriptions of these averaging functions are stored in a replicate average function table 468.

Figure 5A:
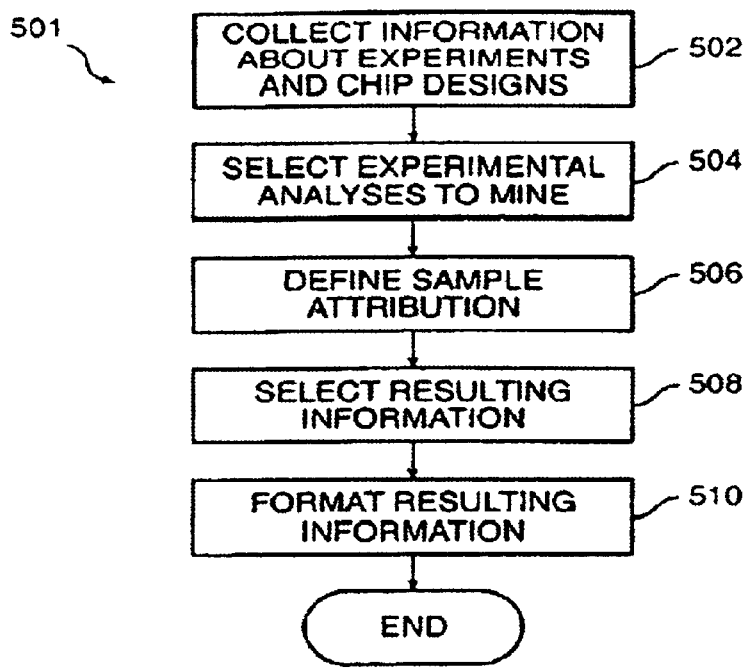
FIGS. 5A–5B depict simplified flowcharts of representative process steps in select embodiments according to the invention.

FIG. 5A illustrates a flowchart 501 of simplified process steps in a particular representative embodiment according to the invention for mining a plurality of experiment information for a pattern. This diagram is merely an illustration and should not limit the scope of the claims herein. One of ordinary skill in the art would recognize other variations, modifications, and alternatives. In a step 502, information from experiments and chip designs is collected. Then, in a step 504, experimental analyses to mine are selected. In a step 506, one or more sample attributions are defined. In a step 508, resulting information is determined from the experimental analyses by mining to form a plurality of resulting information. This resulting information can include one or more resulting gene sets. Finally, a step 510 formats the resulting information for viewing by a user. The combination of these steps can provide to the user the ability access experiment information.

Figure 5B:
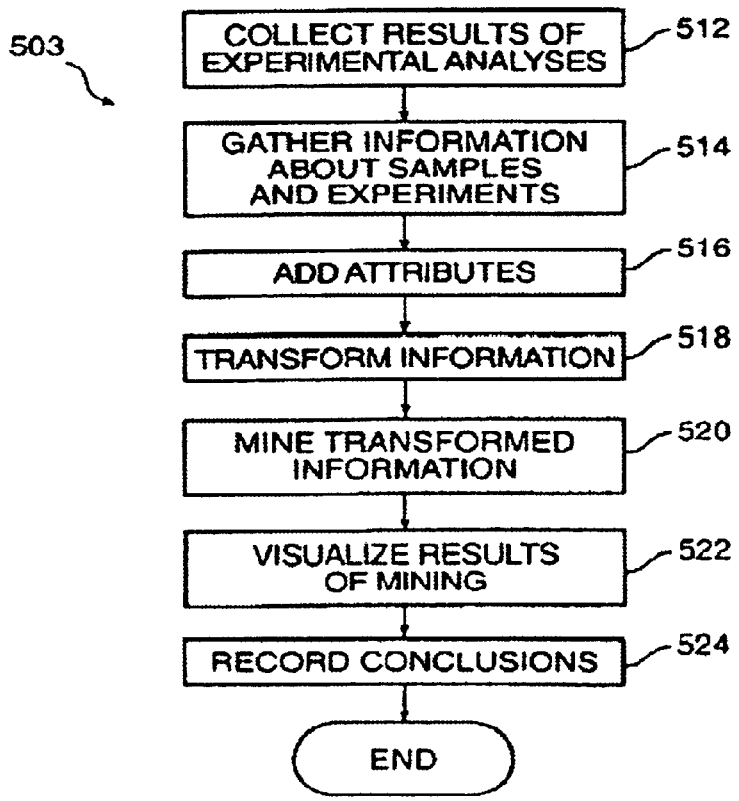

FIG. 5B illustrates a flowchart 503 of simplified process steps in an alternative embodiment according to the invention for working with expression information. This diagram is merely an illustration and should not limit the scope of the claims herein. One of ordinary skill in the art would recognize other variations, modifications, and alternatives. In a step 512, information about a plurality of results of a plurality of experimental analyses is collected. Then, in a step 514, information about samples and information about the plurality of experiments is gathered. Next, in a step 516, one or more attributes are added to the information about the experiments. Then, in a step 518, the plurality of results of experiments information is transformed to form a plurality of transformed information. Transformation can comprise normalization, denormalization, scaling, aggregation, and the like. Subsequently, in a step 520, the plurality of transformed information is mined. Then, in a step 522, the results of the mining are visualized for display to the user. Finally, in a step 524, conclusions are recorded.

Figure 6A:
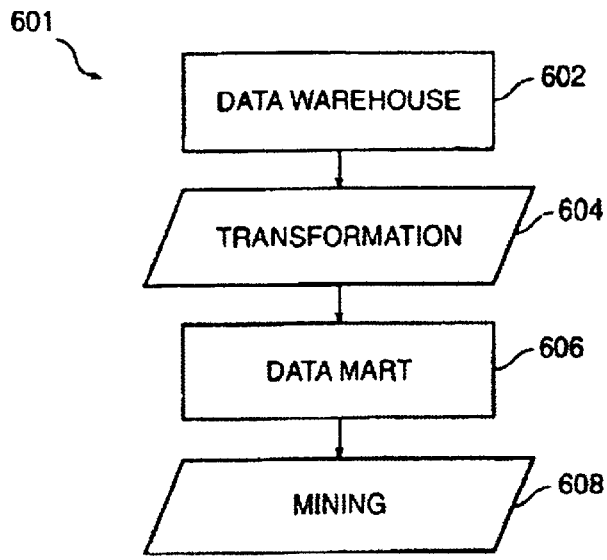
FIGS. 6A–6F illustrate representative block flow diagrams in a particular embodiment according to the present invention.

FIG. 6A illustrates a representative block flow diagram of a simplified process steps in a particular embodiment according to the present invention. This diagram is merely an illustration and should not limit the scope of the claims herein. One of ordinary skill in the art would recognize other variations, modifications and alternatives. Block flow diagram 601 includes an input data warehouse 602, a transformation step 604 to produce an output data mart 606 and a mining process step 608. Input data warehouse 602 can comprise a laboratory information management system and other databases. Data warehouse 602 in a particular embodiment can include genomic information and chip design information, as well as other useful information in the laboratory expression analysis process.

Figure 6B:
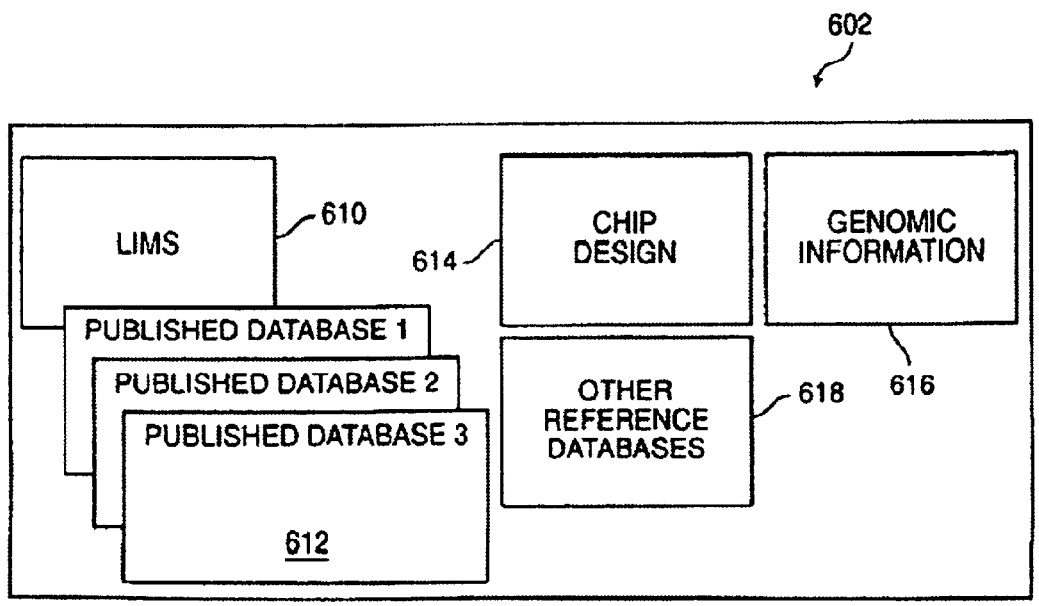

FIG. 6B illustrates a simplified block diagram of a representative data warehouse such as data warehouse 602 of FIG. 6A in a particular embodiment according to the present invention. This diagram is merely an illustration and should not limit the scope of the claims herein. One of ordinary skill in the art would recognize other variations, modifications and alternatives. Data warehouse 602 comprises a laboratory information management system 610 and a plurality of published databases including published database 612. In one particular embodiment, a chip design component 614 can also be included in data warehouse 602. Yet further, genomic information component 616 can also be a part of data warehouse 602. In some embodiments, other reference databases 618 can also be part of data warehouse 602. Many embodiments can also include other information or may omit any of these particular components without departing from the scope of the present invention.

Data transformation step 604 of FIG. 6A can comprise in a particular embodiment according to the present invention a normalization and adjustment step. Normalization and adjustment can include functions tracked by analysis type and/or functional type. In some embodiments, a VBA function or independent applet can be added or removed. Additionally, in many embodiments, a user may selectively omit some transformations according to a preference. Data transformation step 604 can include a replicate step in which a user can manipulate replicates in ways similar to normalizations and adjustments. Further, in many embodiments a user can identify derivation-type replicates using a sample identification. Yet further, in some embodiments, custom selection of replicates can be embedded in an applet.

Figure 6C:
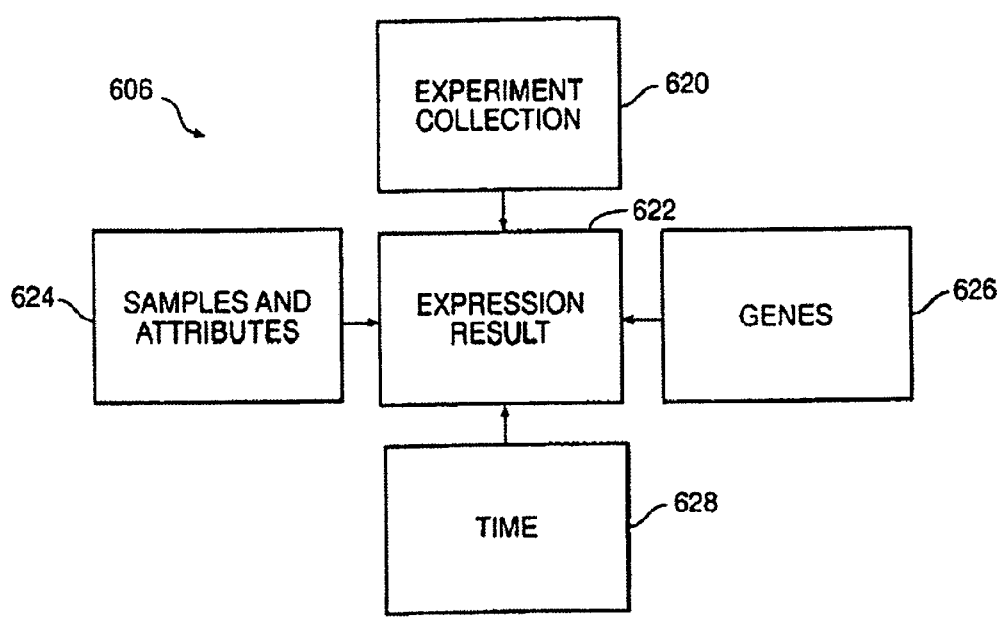

FIG. 6C illustrates a representative data mart such as data mart 606 of FIG. 6A in a particular embodiment according to the present invention. This diagram is merely an illustration and should not limit the scope of the claims herein. One of ordinary skill in the art would recognize other variations, modifications and alternatives. Representative data mart 606 can comprise an experiment collection 620. Information and results of the experiment collection can be forwarded to an expression result 622. In many embodiments, a plurality of samples 624, which can have one or more sample attributes, can further have a relationship to expression result 622. A plurality of genes 626 can also be included in data mart 606. Finally, in a presently preferable embodiment, time may be treated as a dimension 628 of expression result 622. Other methods of organizing data in data marts can also be used without departing from the scope of the present invention.

In a particular embodiment, experiments can be added to or removed from experiment collection 620. Further, in many embodiments, the same experiment collection can be mined for a plurality of purposes. Yet further, experiment collection 620 can be subdivided into one or more subsets of experiments to be mined.

Figure 6D:
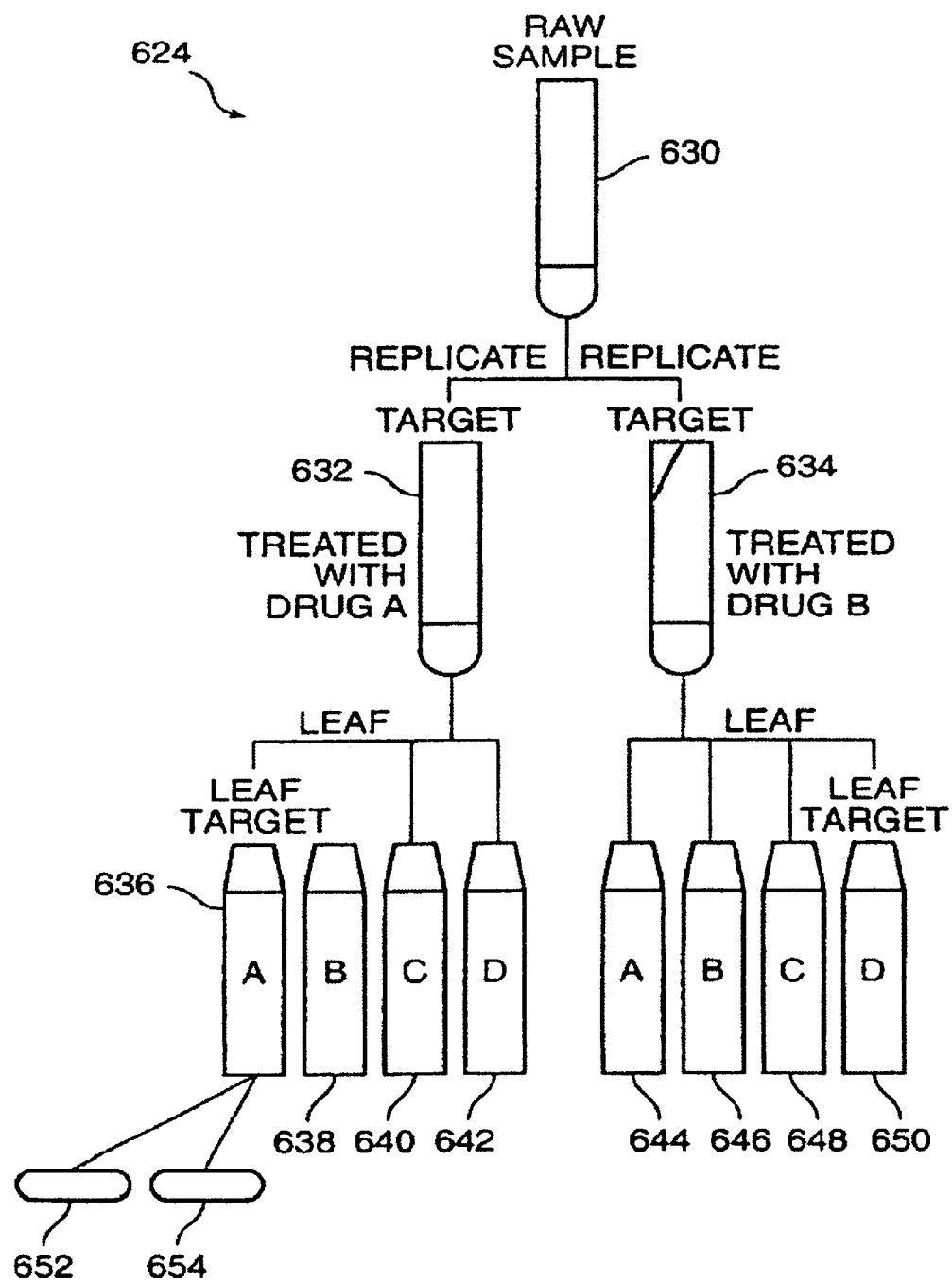

FIG. 6D illustrates a representative organization of samples and targets such as samples 624 of FIG. 6C in a particular embodiment according to the present invention. This diagram is merely an illustration and should not limit the scope of the claims herein. One of ordinary skill in the art would recognize other variations, modifications and alternatives. Samples and targets can allow a user to describe stages of an experiment. At a top level is a raw sample. FIG. 6D illustrates sample 624 that comprises a raw sample 630. Below the raw sample are one or more replicates. Two replicates, a replicate 632 and a replicate 634 comprise raw sample 630. Replicates can comprise targets. Replicate 632 is a target treated with a drug A. Replicate 634 is a target treated with drug B. One or more leaf targets can comprise a target. For example, leaf targets 636, 638, 640 and 642 comprise target 632. Leaf targets 644, 646, 648 and 650 comprise target 634. Experimental analyses can be associated with the leaf targets. FIG. 6D illustrates an experimental analysis 652 and an experimental analysis 654 associated with leaf target 632. In a presently preferable embodiment, experimental analyses can be recursively defined, i.e., an experimental analysis can comprise one or more experimental analyses. In a particular embodiment, intermediate levels can be defined by the user. Other levels can be included and other organizations may be used without departing from the scope of the claims of the present invention.

Figure 6E:
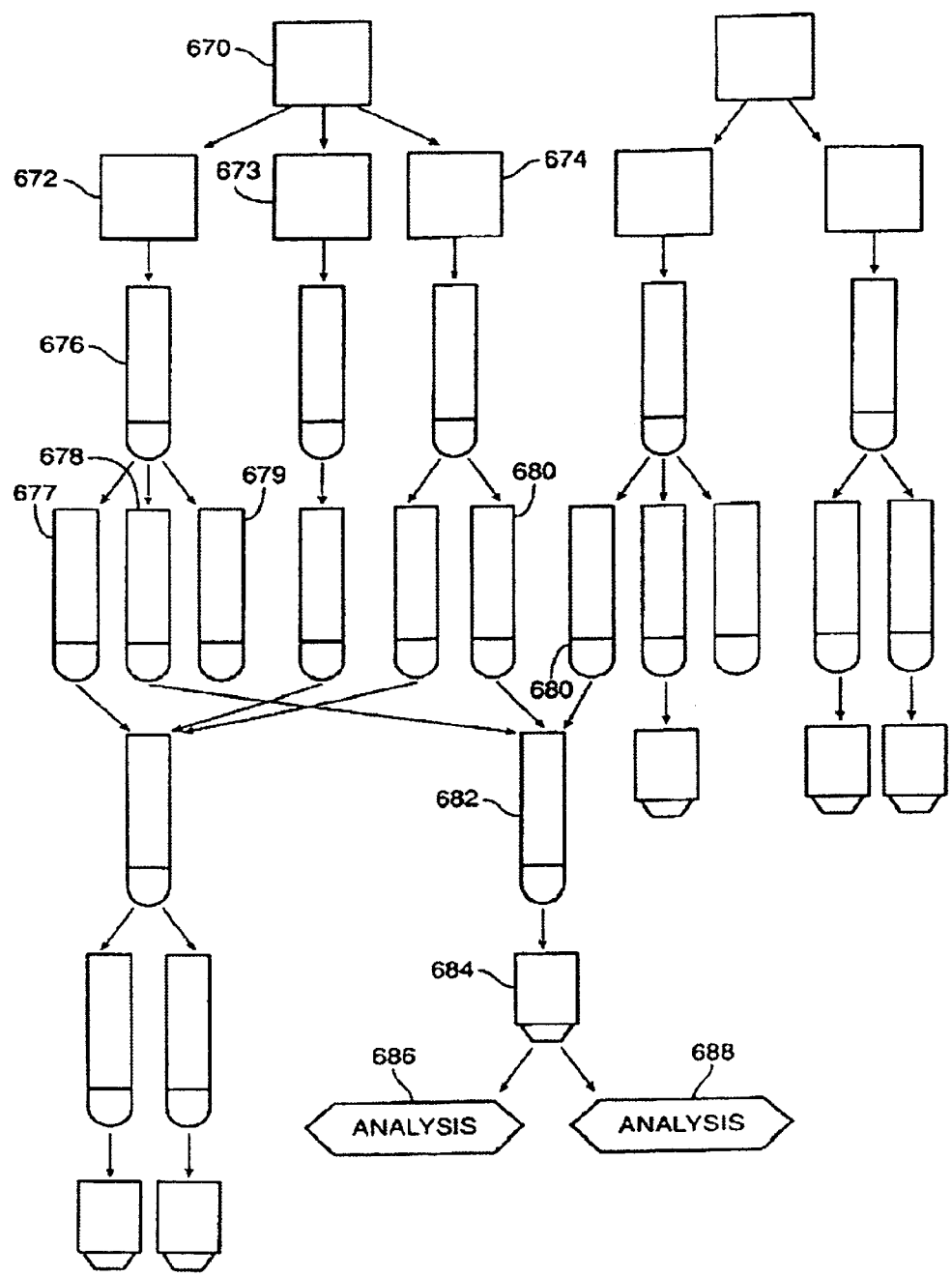

FIG. 6E illustrates another representative organization of samples and targets such as samples 624 of FIG. 6C in a particular embodiment according to the present invention. This diagram is merely an illustration and should not limit the scope of the claims herein. One of ordinary skill in the art would recognize other variations, modification and alternatives. FIG. 6E illustrates a raw sample 670 that represents a piece of extracted tissue, for example. Raw sample 670 has been cleaved into multiple raw samples, such as raw samples 672, 673 and 674. The raw samples are the input to sample preparation system 114 of FIG. 1. Sample preparation system 114 prepares targets, such as target 676 corresponding to raw sample 672. The target can be a fluid including mRNA or other expression indicator. Target 672 has been split into multiple replicates, such as replicates 677, 678 and 679. Replicates 678 and 680 have been pooled to form another target, target 682. The individual "targets" that are applied to chips are the leaf target samples. Each application of a "leaf target sample" to a chip represents an experiment. Leaf target sample 684 is an example. In a presently preferable embodiment, one or more experimental analyses can be associated with a particular leaf target sample. Here, analyses 686 and 688 are associated with leaf target sample 684. Further, an experimental analyses can be defined in terms of one or more other experimental analyses.

Figure 6F:
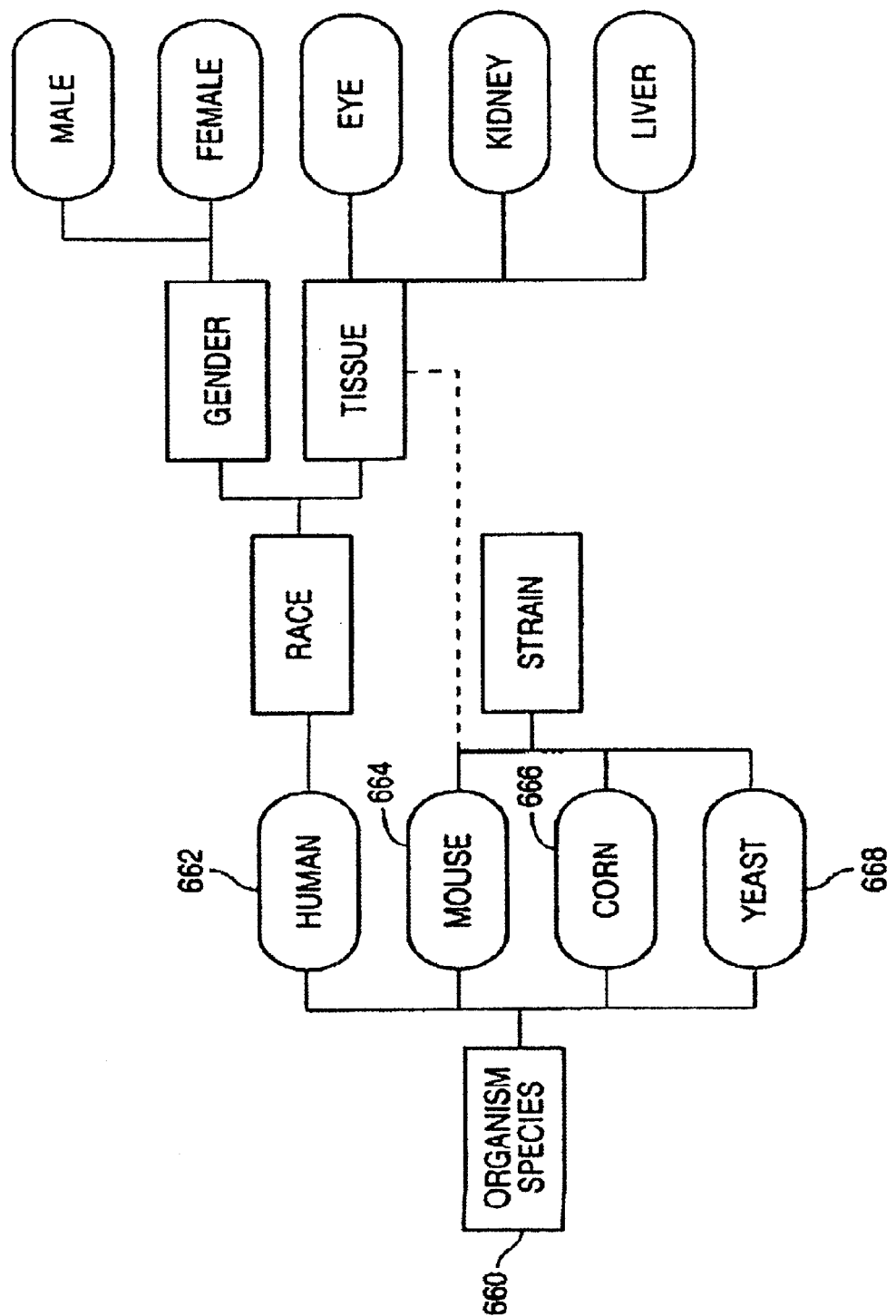

FIG. 6F illustrates a representative organization of a plurality of attributes such as attribute 628 of FIG. 6C in a particular embodiment according to the present invention. This diagram is merely an illustration and should not limit the scope of the claims herein. One of ordinary skill in the art would recognize other variations, modification and alternatives. FIG. 6F illustrates a plurality of attributes having a non-hierarchical structure. In a presently preferable embodiment, an unlimited number of attributes can be assigned to any particular sample. Yet further, different samples can have the same attributes. FIG. 6F illustrates an organism species 660 having a relationship with a plurality of attributes such as human attribute 662, mouse attribute 664, corn attribute 666 and yeast attribute 668. The "strain" and "race" windows are examples of attributes. Other arrangements and attributes can be used in various embodiment without departing from the scope of the claims of the present invention.

In some embodiments, genes 626 of FIG. 6C can be combined into one or more gene sets. Gene sets can be described by various users and in at least one particular embodiment are not shared among users, but can be shared by users in other embodiments. A user can copy other users' gene sets and can edit or delete gene sets. In a presently preferable embodiment, gene sets can be created or saved during mining of the data mart. In some embodiments, one or more functional operations, such as logical operations like union and intersection, arithmatic operations, such as additions, subtractions, scaling, and the like, can be applied to gene sets.

Figure 7A:
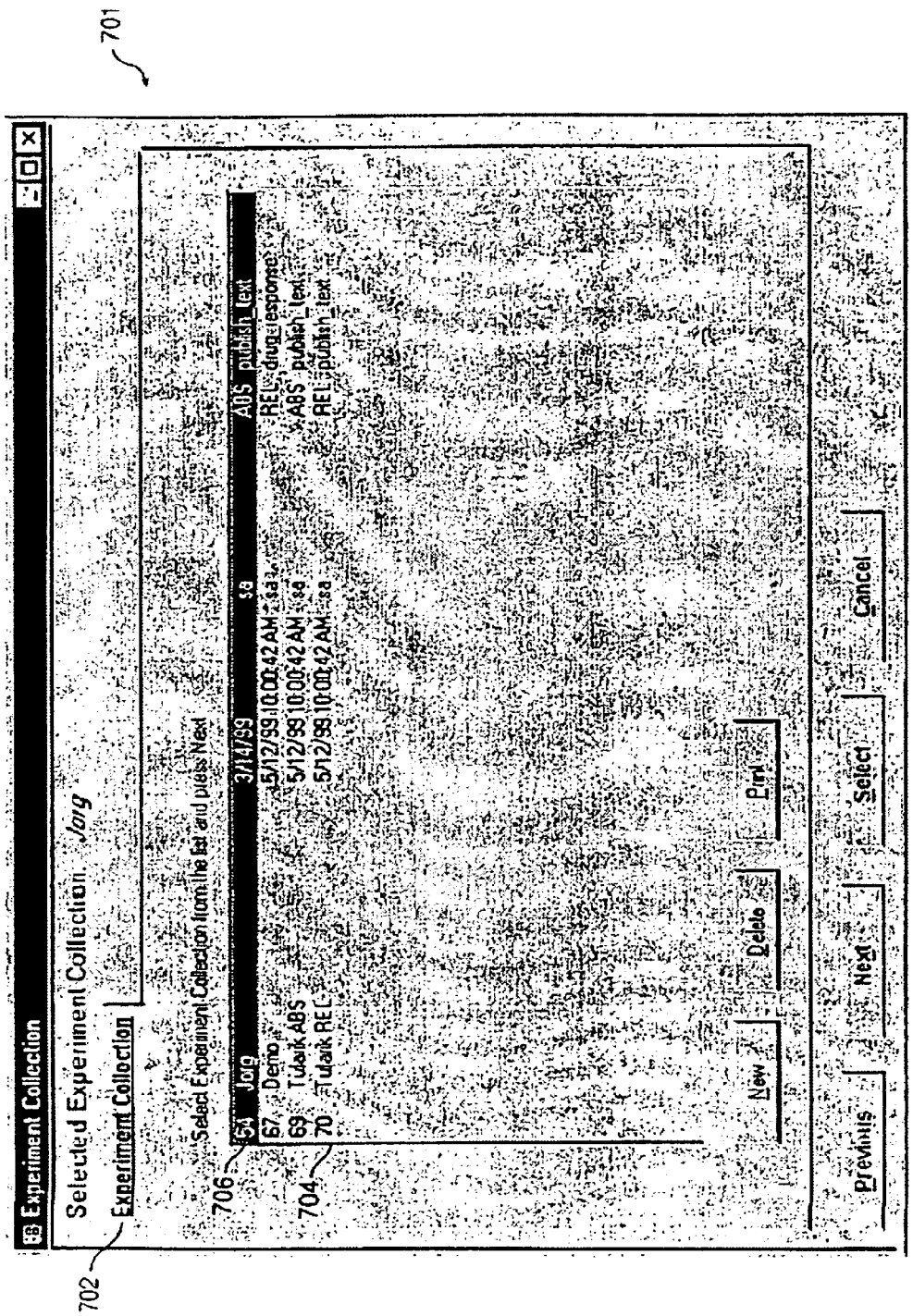
FIGS. 7A–7O illustrate representative user interface screens in a particular embodiment according to the present invention.

FIG. 7A illustrates a representative experiment collection screen 701 of a user interface in a particular embodiment according to the present invention. This diagram is merely an illustration and should not limit the scope of the claims herein. One of ordinary skill in the art would recognize other variations, modifications and alternatives. Screen 701 enables a user to interact with an experiment collection comprised in expression mining database 124 of FIG. 1. Screen 701 comprises an experiment collection selection tab 702 shown with four experiment collections, such as experiment collections 704 and 706. Other experiment collections can be added as needed. Other formats can also be used for presenting this information to a user in various embodiments according to the present invention.

Figure 7B:
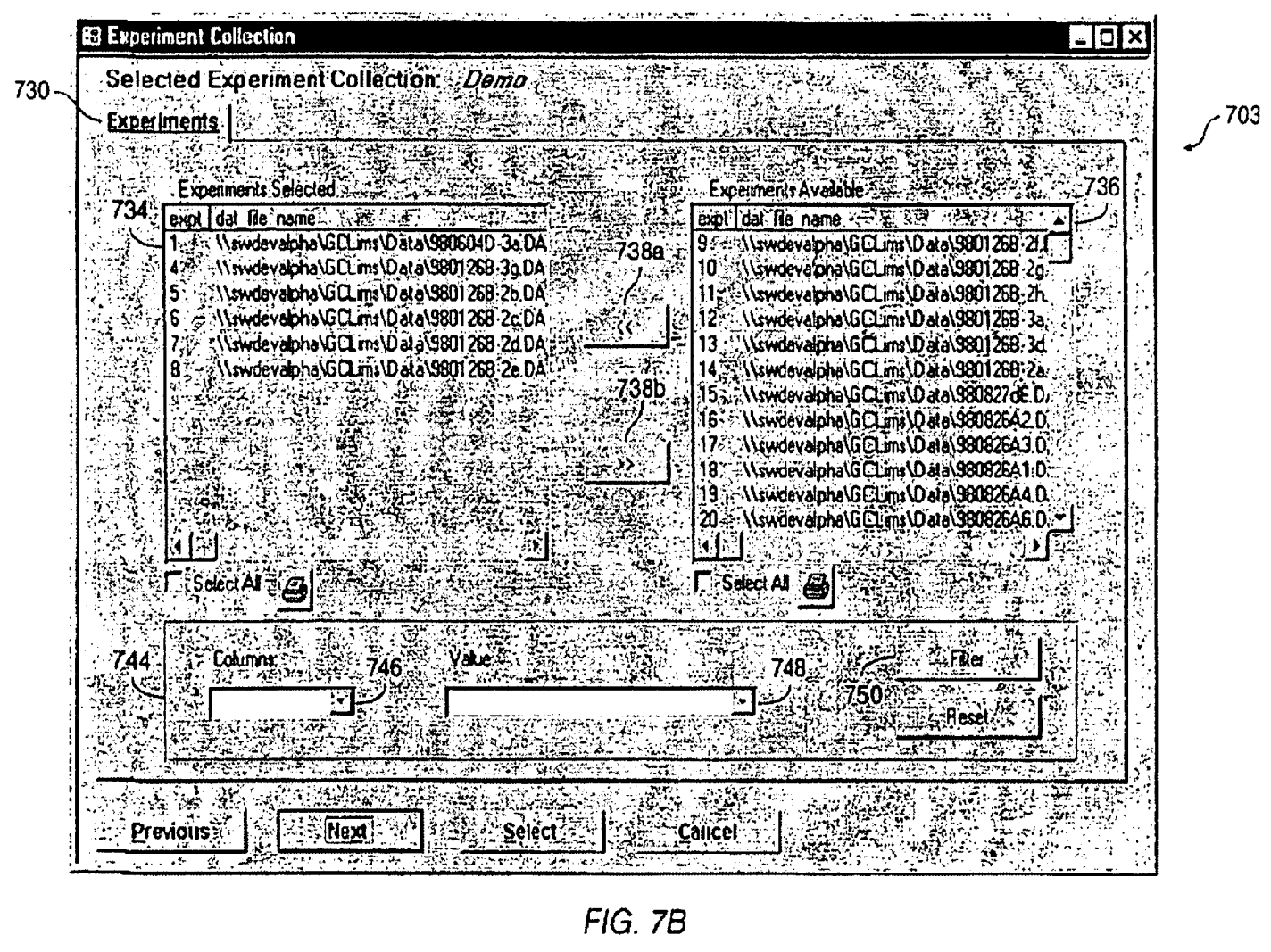

FIG. 7B illustrates an experiment selection screen 703 in a particular embodiment according to the present invention. This diagram is merely an illustration and should not limit the scope of the claims herein. One of ordinary skill in the art would recognize other variations, modifications and alternatives. Experiment selection screen 703 comprises an experiment tab 730. A plurality of experiments is indicated in two scrolling windows, an experiments selected window 734 and an experiments available window 736. Selection buttons 738a and 738b enable various experiments to be moved between experiment scrolling selection window 734 and 736. Experiment selection window 736 includes a plurality of experiments. One or more filters may be applied to the experiment data to limit the number of experiments depicted in experiment scrolling selection windows 734 and 736 using the filter mechanism at the bottom of the screen. The filter mechanism 744 comprises a column selection field 746 and a selection value input field 748. A user may select a particular field for which to screen experiments using column selection field 746 and then enter a desired value in value input field 748. Then, by clicking filter button 750, the user can apply the filter to the experiments in the collection so that only experiments in which the column is set to the selected value will be detected in experiment selection scroll windows 734 and 736.

Figure 7C:
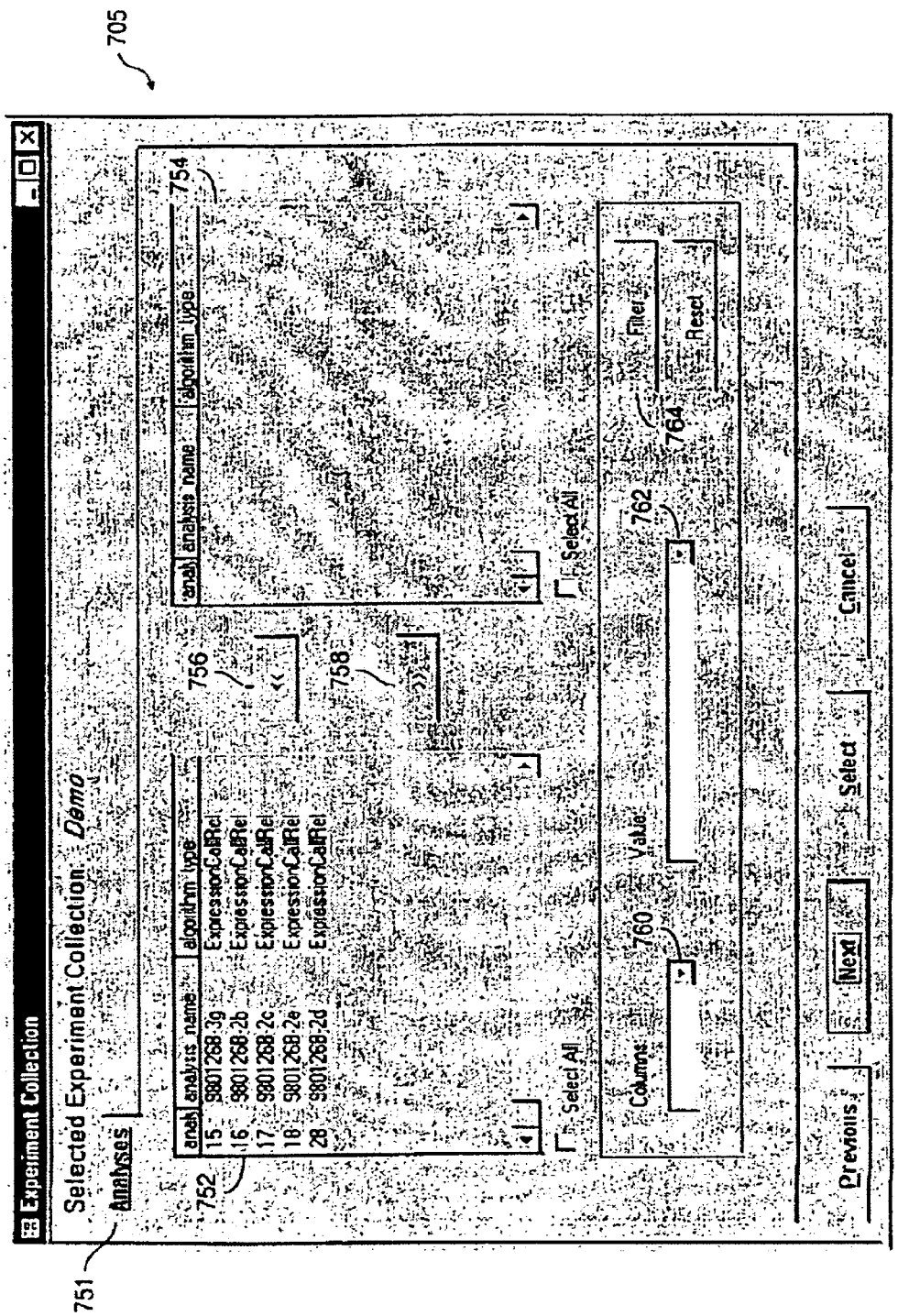

FIG. 7C illustrates a selected experiment collection screen 705 having an analysis tab 751 in a particular embodiment according to the present invention. This diagram is merely an illustration and should not limit the scope of the claims herein. One of ordinary skill in the art would recognize other variations, modifications and alternatives. Screen 705 comprises two scrolling selection windows, an analyses selected window 752 and an analyses available window 754. Selection keys 756 and 758 may be used to move various analyses between scrolling selection windows 752 and 754. Similarly, a filter mechanism provided at the bottom of screen 705 enables a user to screen the analyses depicted in scrolling selection windows 752 and 754 by selecting a particular column using column selection field 760 and inputting a desired value into value input field 762 and then clicking filter button 764 to apply the filter to the analyses in the experiment collection.

Figure 7D:
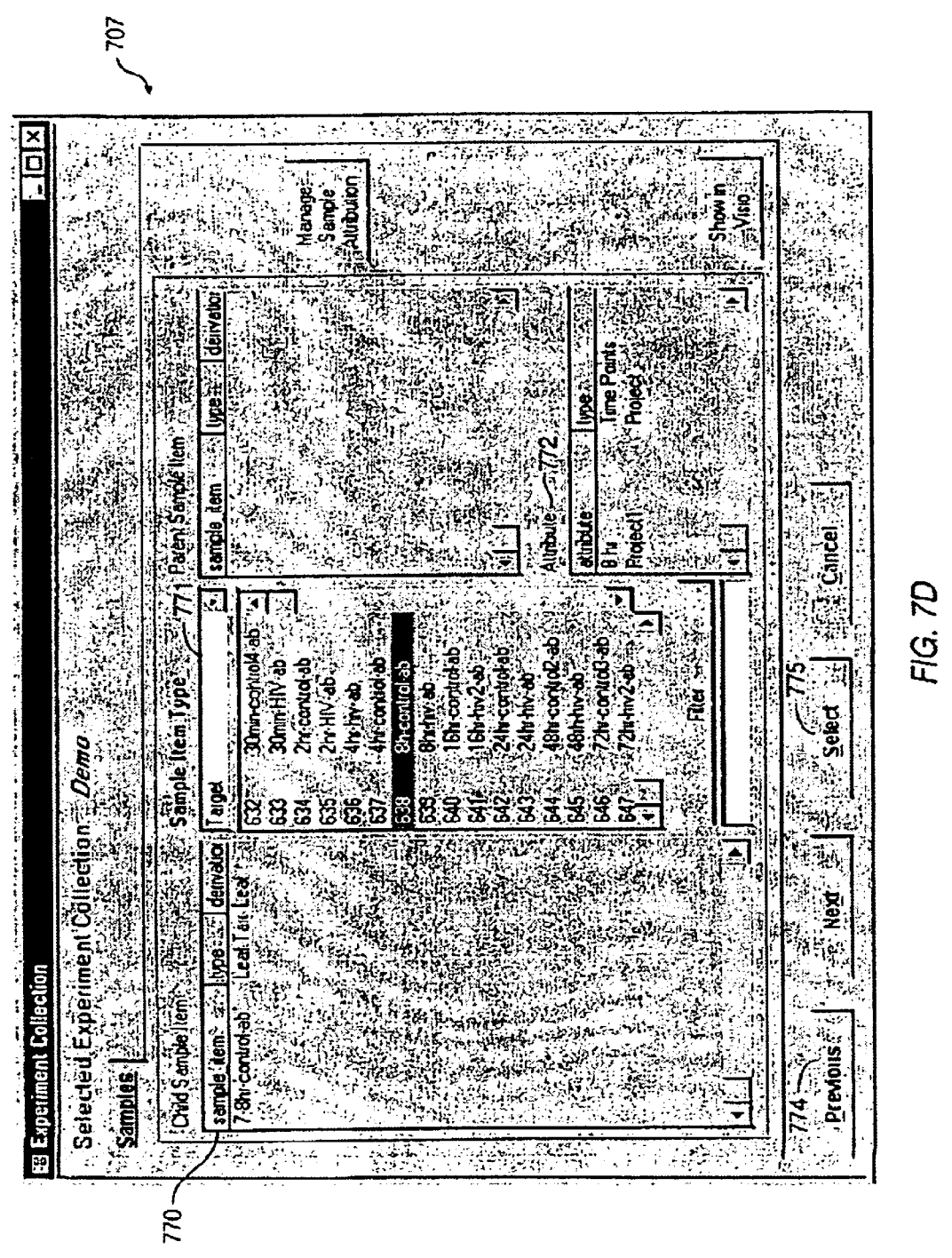

FIG. 7D illustrates a representative sample selection screen 707 in a particular embodiment according to the present invention. This diagram is merely an illustration and should not limit the scope of the claims herein. One of ordinary skill in the art would recognize other variations, modifications and alternatives. Screen 707 enables a user to view the results of selections made on one or more samples. Screen 707 comprises a plurality of selections including a sample selection 770, a sample-type selection 771 and an attribute-type selector 772. A previous/next button pair 774 and a select button 775 enable searching and selecting, respectively.

Figure 7E:
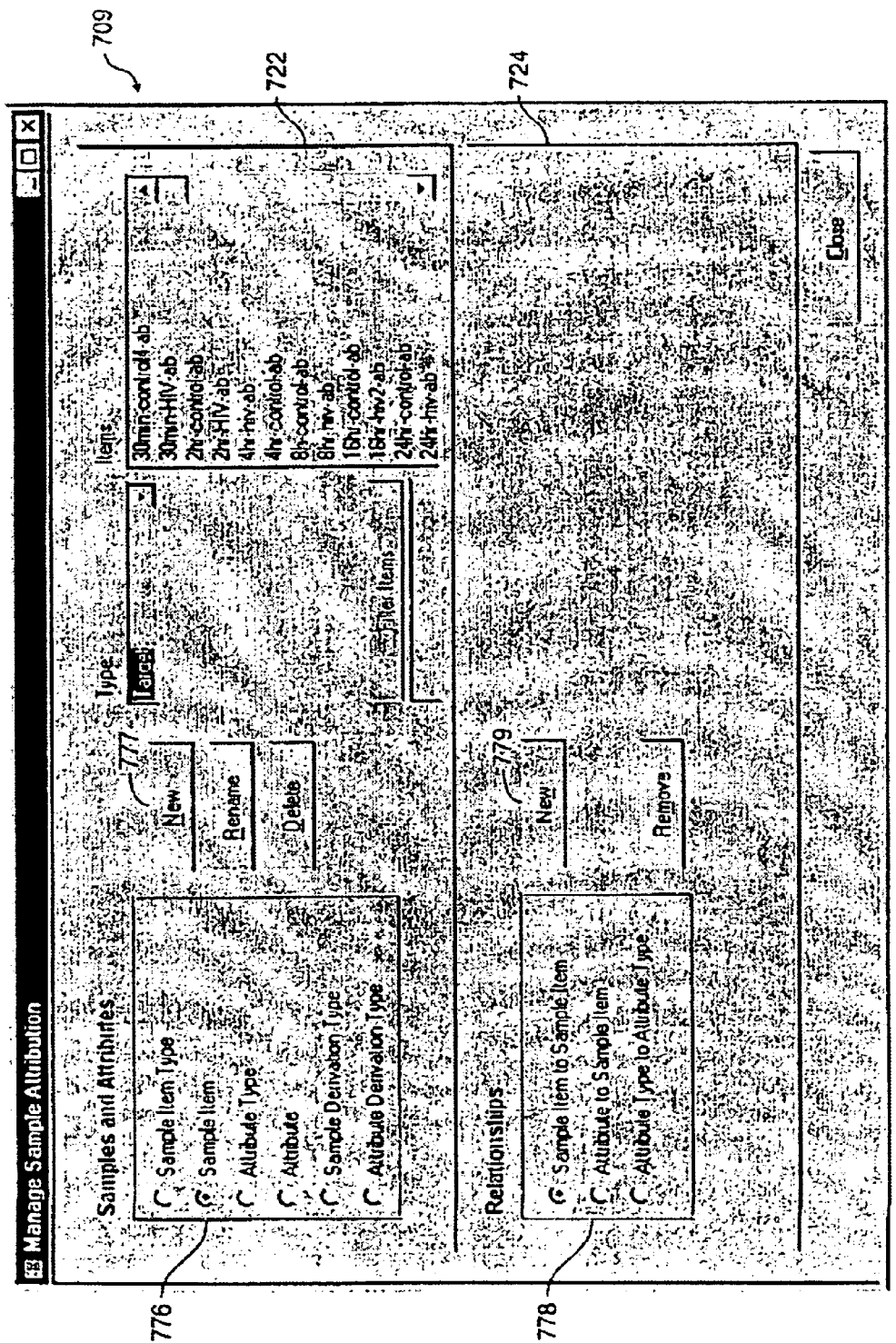
Figure 7F:
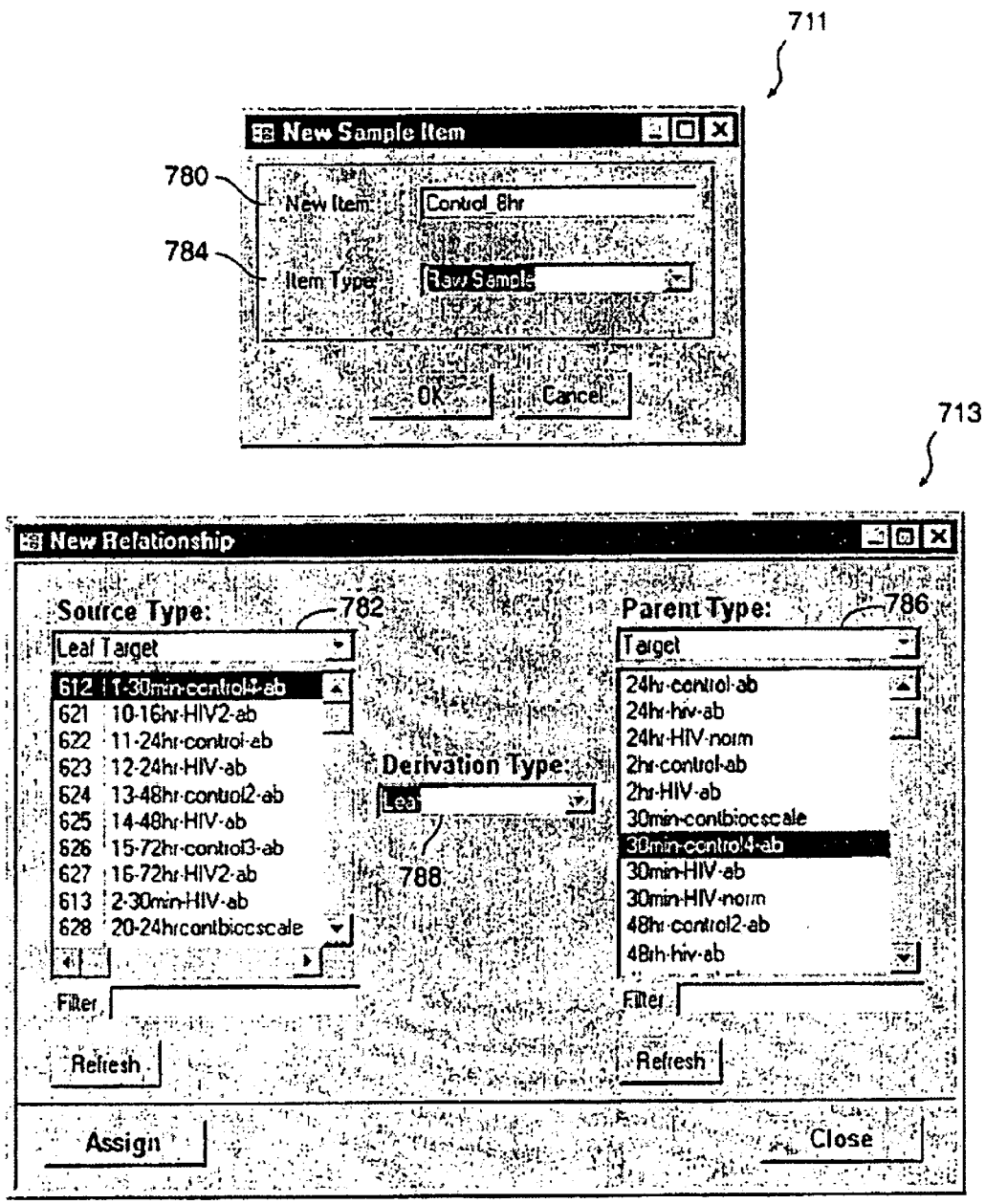

FIG. 7E illustrates a representative sample and attribute management screen 709 in a particular embodiment according to the present invention. This diagram is merely an illustration and should not limit the scope of the claims herein. One of ordinary skill in the art would recognize other variations, modifications and alternatives. Using screen 709, users can add, delete or rename samples, attributes, sample and attribute types and relationships between any of these. Screen 709 comprises a samples and attributes section 722 and a relationships section 724. Item selection window 776 of sample and attribute section 722 provides functions that enable the user to select the type of new item, sample, attribute, and the like. Function buttons 777 enable the user to select operations such as add new, rename, delete and the like. If the user elects to create a new item, then screen 711 of FIG. 7F is displayed. Screen 711 enables the user to create new items. The user can enter a name for the item in a new item field 780 and an item type in item type field 784 of screen 711. Otherwise, the user can work with relationships using the relationship section 724 in screen 709 of FIG. 7E.

Relationship selection window 778 of relationship section 724 enables the user to select the type of relationship, such as a relationship between sample item to sample item, a relationship between attribute and sample item or a relationship between attribute type to attribute type, for example. Function buttons 779 enable the user to select operations such as add new, delete and the like. If the user elects to create a new relationship, then screen 713 of FIG. 7F is displayed. Screen 713 enables the user to create new relationships. The user can enter a source of the relationship in a source window 782, a parent in the parent window 786 and a type of relationship in the derivation type window 788.

Figure 7G:
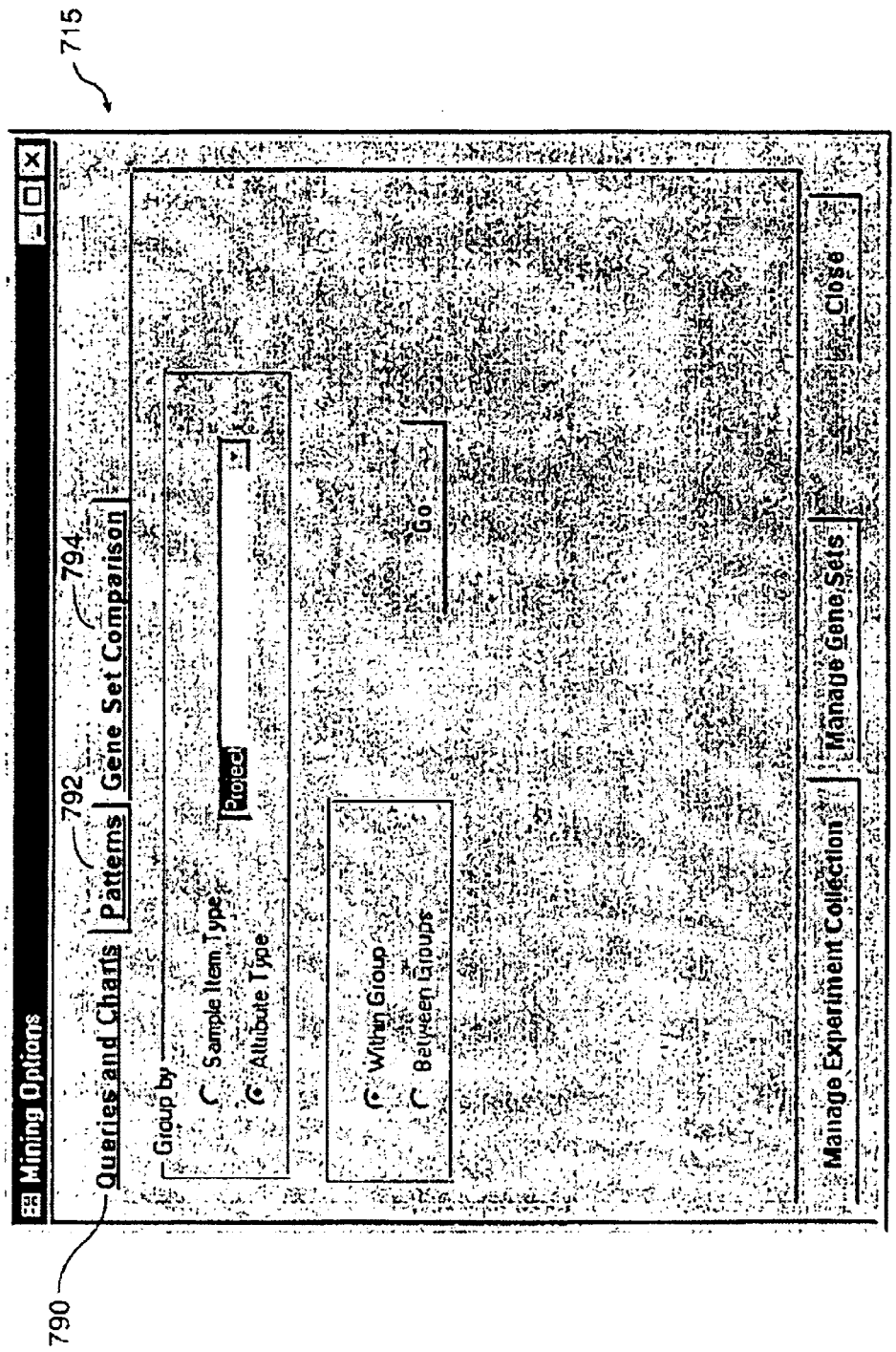

FIG. 7G illustrates a representative data mining option management screen 715 in a particular embodiment according to the present invention. This diagram is merely an illustration and should not limit the scope of the claims herein. One of ordinary skill in the art would recognize other variations, modifications and alternatives. Screen 715 illustrates a plurality of tabs, including a queries and charts tab 790, a patterns tab 792 and a gene set comparison tab 794. The user can specify some grouping parameters using the group by functions of queries and charts tab 790 in order to begin data mining.

Figure 7H:
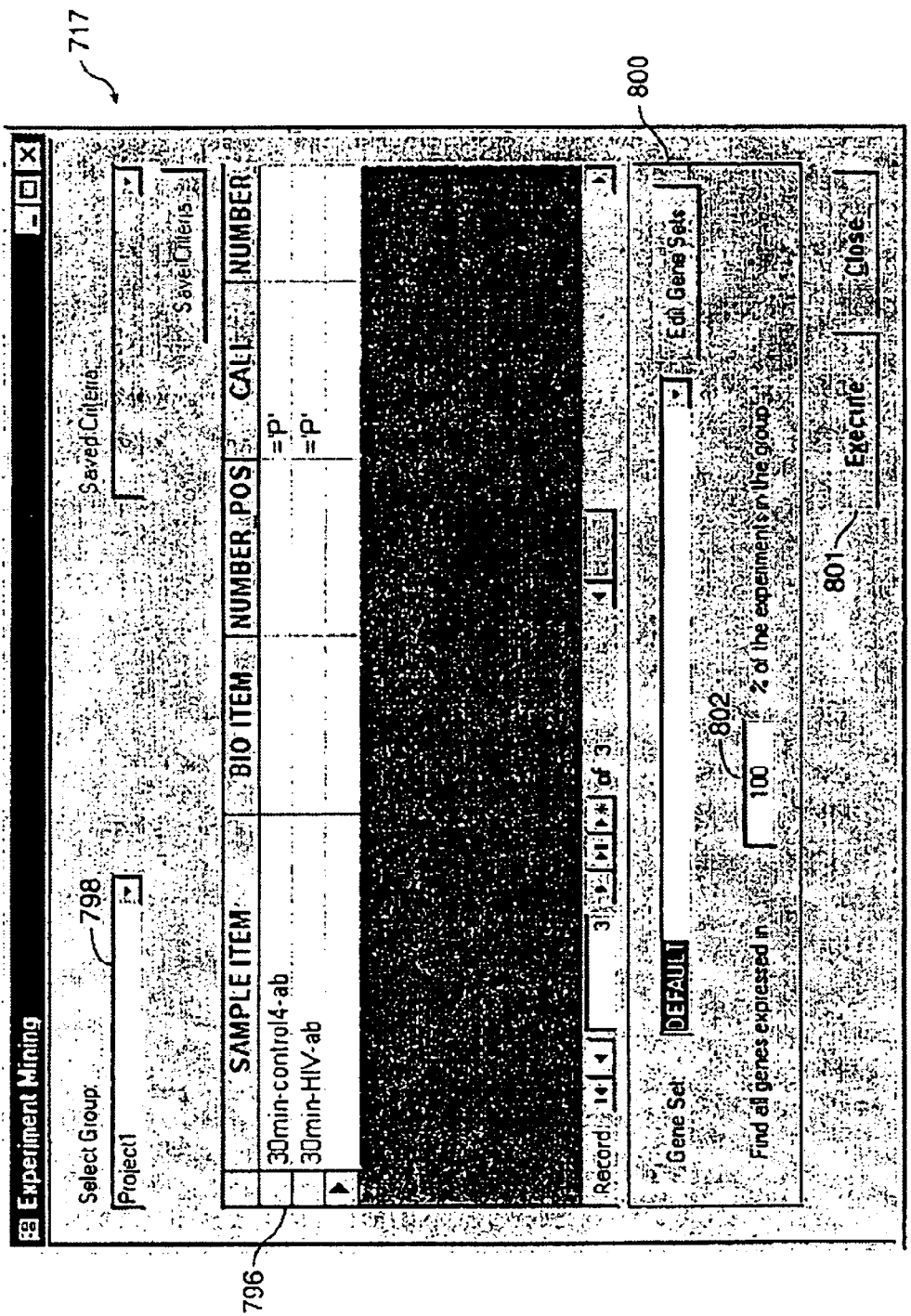

FIG. 7H illustrates an experiment mining screen 717 in a particular embodiment according to the present invention This diagram is merely an illustration and should not limit the scope of the claims herein. One of ordinary skill in the art would recognize other variations, modifications and alternatives. Using the functions of screen 717, users can enter criteria for data selection, such as for example, what gene sets to use and the like. Screen 717 includes a plurality of sample items, such as sample item 796. A group selection field 798 enables a user to select from a plurality of groups in the experiment collection. One or more gene sets can be selected using the gene set selection field 800. Gene sets can be all genes represented by a particular gene chip, or a subset. A default of all gene sets on a particular gene chip is provided in one particular embodiment, but other defaults can be used. A presence measure of the gene expression within the group can be specified using the expression percentage field 802. When the user has specified the search parameters using these fields, depressing the execute button 801 starts the data mining.

FIG. 7I illustrates a selected data screen 719 in a particular embodiment according to the present invention. This diagram is merely an illustration and should not limit the scope of the claims herein. One of ordinary skill in the art would recognize other variations, modifications and alternatives. Data selection screen 719 illustrates the data that meet the criteria specified by the user in experiment mining screen 717 of FIG. 7H. Data selection screen 719 illustrates a plurality of leaf parents, including leaf parent 804. Screen 719 also illustrates experiment replications 805, bio items 806 and results measured 807 during the experiment for each leaf parent. Users can export the results of the mining using export button 808 and/or can save the results of the mining using save gene set button 809.

Figure 7J:
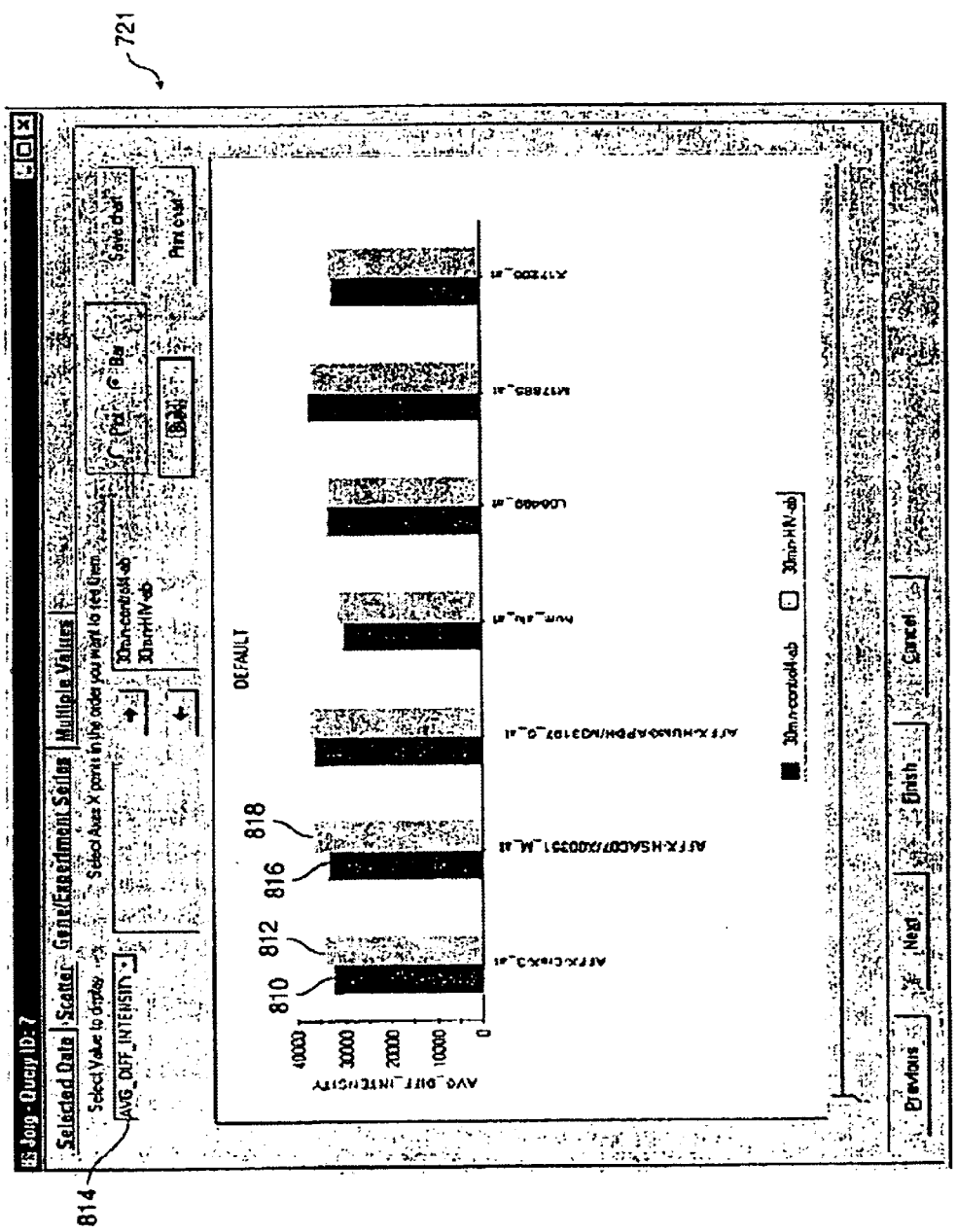

FIG. 7J illustrates a bar chart visualization screen 721 in a particular embodiment according to the present invention. This diagram is merely an illustration and should not limit the scope of the claims herein. One of ordinary skill in the art would recognize other variations, modifications and alternatives. Scatter pot selection visualization screen 721 comprises a display area having a display of the data in the experiment collection. A quantity to be visualized can be selected from select value field 814. Experimental results 810 and 812 indicate differences in expression for a particular gene for the quantity selected by the user with field 814.

Figure 7K:
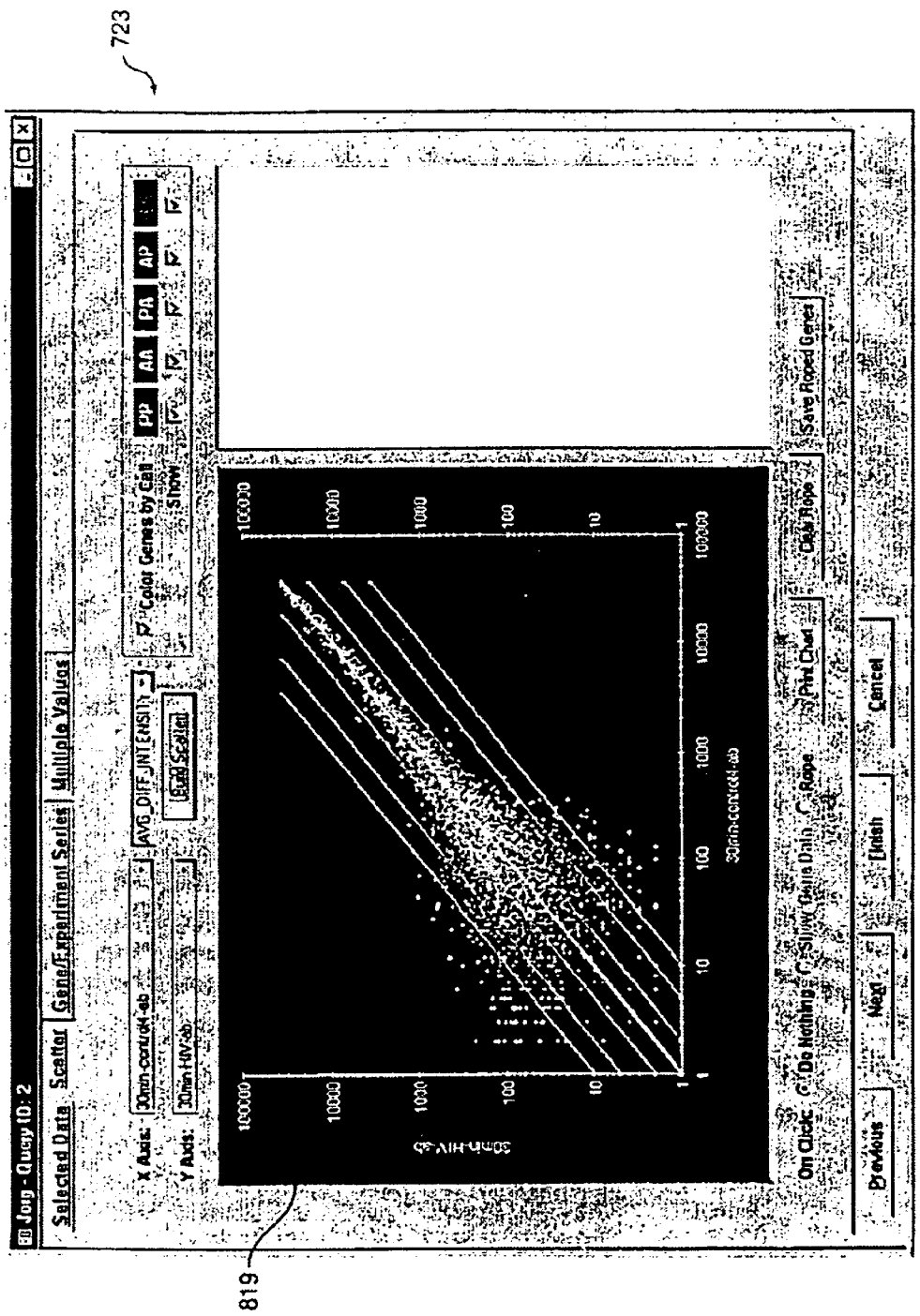

FIG. 7K illustrates a scatter plot visualization screen 723 in a particular embodiment according to the present invention. This diagram is merely an illustration and should not limit the scope of the claims herein. One of ordinary skill in the art would recognize other variations, modifications and alternatives. Scatter pot selection visualization screen 723 comprises a display area 819 having a display of the data in the experiment collection. While display area 819 illustrates an X-Y plot, other forms of data visualization, such as bar charts, graphs, pie-charts and the like, are contemplated by various embodiments according to the present invention.

FIG. 7L illustrates pattern search screens 725 and 727 in a particular embodiment according to the present invention. This diagram is merely an illustration and should not limit the scope of the claims herein. One of ordinary skill in the art would recognize other variations, modifications and alternatives. Gene pattern searching enables the user to determine relationships such as which genes behave similarly when exposed to a certain drug, and the like. Selecting the "pattern" tab on screen 725 displays information entry devices for entering search criteria, including a gene patterns field 820. By specifying search on gene patterns, the user can be presented with gene pattern search screen 727. The user can select a plurality of gene sets to compare using gene set name fields 822 and 824. A measurement selection field 826 enables the user to select a measurement of interest as a basis of the comparison.

FIG. 7M illustrates gene set comparison screens 729 and 731 in a particular embodiment according to the present invention. This diagram is merely an illustration and should not limit the scope of the claims herein. One of ordinary skill in the art would recognize other variations, modifications and alternatives. Gene set comparisons enable the user to determine relationships such as which gene sets include particular genes, exclude particular genes, or functional combinations of genes. Selecting the "gene set comparison" tab on screen 729 displays information about gene sets that can be selected by the user for comparison. Screen 729 illustrates a plurality of gene sets, including gene sets 830, 832 and 834. After specifying gene sets of interest, the user can be presented with gene comparison screen 731. The user can select a plurality of genes as bases of comparing the gene sets selected in screen 720 by checking one or more of a plurality of selection windows, such as selection windows 836 and 838.

FIGS. 7N–7O illustrate sample data management screens 733 and 735 in particular embodiments according to the present invention. These diagrams are merely illustrations and should not limit the scope of the present invention. One of ordinary skill in the art would recognize other variations, modifications and alternatives. FIG. 7N illustrates gene set management screen 733. This screen enables the user to perform a variety of tasks with genes and gene sets, such as add, remove, create and copy gene sets, and add and remove genes within gene sets, and the like. FIG. 7O illustrates update gene set screen 735. This screen enables the user to specify one or more genes to be removed from the database.

In conclusion the present invention provides a method for mining experiment information for a patterns selectable by a user. One advantage is that the method provides better access to genetic expression information than methods known in the prior art. Another advantage provided by this approach is that the results of numerous experiments can be mined effectively using visualization techniques and set theory queries, for example.

It is understood that the examples and embodiments described herein are for illustrative purposes only and that various modifications or changes in light thereof will be suggested to persons skilled in the art and are to be included within the spirit and purview of this application and scope of the appended claims. For example, tables may be deleted, contents of multiple tables may be consolidated, or contents of one or more tables may be distributed among more tables than described herein to improve query speeds and/or to aid system maintenance. Also, the database architecture and data models described herein are not limited to biological applications but may be used in any application. All publications, patents, and patent applications cited herein are hereby incorporated by reference.

What is claimed is:

1. A computer based method for mining a plurality of experiment information for a pattern, said method comprising:

collecting information from experiments and chip designs;

selecting from said experiments and said chip designs ones to be mined;

defining at least one of a plurality of groupings for said experiments to be mined;

selecting based upon said at least one of a plurality of groupings, information about said plurality of experiments to be mined, forming a plurality of resulting information, said plurality of resulting information including at least a resulting gene set; and formatting said plurality of resulting information for viewing by a user.

2. The method of claim 1 wherein experiments to be mined are selected based upon at least one of a plurality of experimental analyses.

3. The method of claim 1 wherein said at least one of a plurality of groupings is a sample type.

4. The method of claim 1 wherein said at least one of a plurality of groupings is a sample attribute.

5. The method of claim 1 wherein said plurality of groupings are sample attributes having a non-hierarchical arrangement.

6. The method of claim 1 further comprising adding experiments to said experiments to be mined.

7. The method of claim 1 further comprising deleting experiments to said experiments to be mined.

8. The method of claim 1 wherein said pattern is a gene pathway.

9. The method of claim 1 wherein said pattern is a drug toxicity.

10. The method of claim 1 further comprising enabling a user to apply set theory operations on said resulting gene sets.

11. A computer based method for working with expression information, said method comprising:
    collecting information about a plurality of results of a plurality of experiments;
    gathering information about samples and information about said plurality of experiments;
    adding at least one of a plurality of attributes to said information about said plurality of experiments;
    transforming said plurality of results of experiments, to form a plurality of transformed information;
    mining said plurality of transformed information; and
    visualizing said plurality of transformed information.

12. The method of claim 11 wherein said information about said plurality of experiments comprises at least one of a plurality of experimental analyses.

13. The method of claim 12 wherein said at least one of a plurality of experimental analyses comprises one or more experimental analyses.

14. The method of claim 11 wherein said transforming comprises normalizing and said transformed information comprises normalized information.

15. The method of claim 11 further comprising recording one or more results of said mining said plurality of transformed information.

16. The method of claim 11 further comprising citing theories about said transformed information.

17. A computer program product for mining a plurality of experiment information for a pattern, said computer program product comprising:
    code for collecting information from experiments and chip designs;
    code for selecting a subset of said experiments and said chip designs, said subset being a plurality of experiments to be mined;
    code for defining at least one of a plurality of groupings for said experiments to be mined;
    code for selecting based upon said at least one of a plurality of groupings, information about said plurality of experiments to be mined, to form a plurality of resulting information, said plurality of resulting information including at least a resulting gene set;
    code for formatting said plurality of resulting information for viewing by a user; and
    a computer readable storage medium for containing the codes.

18. The program product of claim 17 wherein said at least one of a plurality of groupings is a sample type.

19. The computer program product of claim 17 wherein said at least one of a plurality of groupings is a sample attribute.

20. The computer program product of claim 17 wherein said plurality of groupings are sample attributes having a non-hierarchical arrangement.

21. The computer program product of claim 17 further comprising code for adding experiments to said experiments to be mined.

22. The computer program product of claim 17 further comprising code for deleting experiments to said experiments to be mined.

23. The computer program product of claim 17 wherein said pattern is a gene pathway.

24. The computer program product of claim 17 wherein said pattern is a drug toxicity.

25. The computer program product of claim 17 further comprising code for enabling a user to apply set theory operations on said resulting gene sets.

26. A computer program product for working with expression information, said computer program product comprising:
    code for collecting information about a plurality of results of a plurality of experiments;
    code for gathering information about samples and information about said plurality of experiments;
    code for adding at least one of a plurality of attributes to said information about said plurality of experiments;
    code for transforming said plurality of results of experiments, to form a plurality of transformed information;
    code for mining said plurality of transformed information;
    code for visualizing said plurality of transformed information; and
    a computer readable storage medium for storing the codes.

27. The computer program product of claim 26 further comprising code for citing theories about said transformed information.

28. The computer program product of claim 26 wherein said code for transforming further comprises code for normalizing and said transformed information further comprises normalized information.

29. A system for managing expression information comprising:
    a database;
    a computer memory; and
    a processor, said processor operatively disposed to:
        collect information about a plurality of results of a plurality of experiments;
        gather information about samples and information about said plurality of experiments;
        add at least one of a plurality of attributes to said information about said plurality of experiments;
        transform said plurality of results of experiments, to form a plurality of transformed information;
        mine said plurality of transformed information; and
        visualize said plurality of transformed information.

* * * * *